United States Patent
Ueno et al.

(10) Patent No.: US 7,410,786 B2
(45) Date of Patent: Aug. 12, 2008

(54) SULFATED FUCOGALACTAN DIGESTING ENZYME GENE

(75) Inventors: Harumi Ueno, Shiga (JP); Jun Tomono, Shiga (JP); Hiroaki Sagawa, Shiga (JP); Takeshi Sakai, Aomori (JP); Ikunoshin Kato, Shiga (JP)

(73) Assignee: Takara Bio. Inc., Shiga (JP)

( * ) Notice: Subject to any disclaimer, the term of this patent is extended or adjusted under 35 U.S.C. 154(b) by 0 days.

(21) Appl. No.: 11/681,453

(22) Filed: Mar. 2, 2007

(65) Prior Publication Data

US 2007/0148752 A1 Jun. 28, 2007

Related U.S. Application Data

(62) Division of application No. 10/487,097, filed as application No. PCT/JP02/09010 on Sep. 5, 2002, now Pat. No. 7,217,552.

(30) Foreign Application Priority Data

Sep. 5, 2001 (JP) ............................. 2001-268250

(51) Int. Cl.
*C12N 9/24* (2006.01)
*C12N 1/20* (2006.01)
*C12P 19/04* (2006.01)
*C12P 21/06* (2006.01)
*C12Q 1/68* (2006.01)
*C07H 21/04* (2006.01)

(52) U.S. Cl. .......................... 435/200; 435/101; 435/6; 435/69.1; 435/252.3; 536/23.2

(58) Field of Classification Search ................. 435/200, 435/101, 6, 252.33, 69.1, 488; 536/23.2
See application file for complete search history.

(56) References Cited

U.S. PATENT DOCUMENTS

| 6,054,577 | A | 4/2000 | Sakai et al. |
| 6,207,652 | B1 | 3/2001 | Sakai et al. |
| 6,489,155 | B1 | 12/2002 | Takayama et al. |
| 6,590,097 | B1 | 7/2003 | Sakai et al. |

FOREIGN PATENT DOCUMENTS

| WO | WO 96/34004 A1 | 10/1996 |
| WO | WO 97/26896 A1 | 7/1997 |
| WO | WO 99/11797 A1 | 3/1999 |
| WO | WO 00/50464 A1 | 8/2000 |

OTHER PUBLICATIONS

Sasaki et al., "Partial Purification and Characterization of an Enzyme Releasing 2-Sulfo-α-L-fucopyranose from 2-Sulfo- α-L-fucopyranosyl-(1-2) Pyridylaminated Fucose from a Sea Urchin, *Strongylocentrotus nudus*", Biosci. Biotech. Biochem., 60 (4), 666-668, 1996.

Usui et al., "Isolation of Highly Purified "Fucoidan" from *Eisenia bicyclis* and Its Anticoagulant and Antitumor Activities", Agric. Biol. Chem. 44 (8), 1965-1966, 1980.

*Primary Examiner*—Richard Hutson
*Assistant Examiner*—Iqbal Chowdhury
(74) *Attorney, Agent, or Firm*—Browdy and Neimark, PLLC

(57) ABSTRACT

A gene encoding a polypeptide having an activity of digesting sulfated fucogalactan which is useful in sugar chain engineering reagents, analyzing the structures of sulfated fucose-containing polysaccharides and preparing degraded products of the polysaccharides; a genetic engineering process for producing the polypeptide; and the polypeptide obtained by the process.

1 Claim, No Drawings

SULFATED FUCOGALACTAN DIGESTING ENZYME GENE

CROSS-REFERENCE TO RELATED APPLICATIONS

The present application is a division of application Ser. No. 10/487,097, filed Feb. 19, 2004, now U.S. Pat. No. 7,217,552 which is a 371 national stage application of PCT/JP02/09010, filed Sep. 5, 2002, which claims priority from JP 2001-268250, filed Sep. 5, 2001. The entire contents of prior applications 10/487,097 and PCT/JP02/09010 are herein incorporated by reference.

TECHNICAL FIELD

The present invention relates to a gene encoding a polypeptide that has an activity of degrading a sulfated fucogalactan which is useful as a reagent for glycotechnology, for a structural analysis of a sulfated fucose-containing polysaccharide or for preparation of a smaller molecule from the polysaccharide, a method for producing the polypeptide using genetic engineering techniques, and a polypeptide obtainable by the method.

BACKGROUND ART

Brown algae contain a variety of sulfated fucose-containing polysaccharides. For example, sulfated fucose-containing polysaccharides such as (1) sulfated fucans consisting of fucose and sulfate groups; (2) sulfated fucoglucuronomannans containing glucuronic acid, mannose, fucose and sulfate groups, e.g., the sulfated fucose-containing polysaccharide-U as described in WO 97/26896 (approximate molar ratio of constituting saccharides, fucose:mannose:galactose: uronic acid:sulfate group=10:7:4:5:20; hereinafter referred to as U-fucoidan); and (3) sulfated fucogalactan consisting of fucose and galactose, e.g., the sulfated fucose-containing polysaccharide-F as described in WO 97/26896 (approximate molar ratio of constituting saccharides, fucose:galactose=10: 1; hereinafter referred to as F-fucoidan), or the sulfated fucose-containing polysaccharide-G as described in WO 00/50464 (approximate molar ratio of constituting saccharides, galactose:fucose=2:1; hereinafter referred to as G-fucoidan) are known. Almost all of these sulfated fucose-containing polysaccharides are macromolecular anions. Therefore, they behave in a chemically and physically similar manner in various purification steps, making it difficult to separate them from each other. For this reason, biological activities of sulfated fucose-containing polysaccharides derived from brown algae have often been examined without separating them from each other. Therefore, it was difficult to identify the sulfated fucose-containing polysaccharide that was responsible for the observed biological activity.

To date, correlation between an activity and a molecule is known for the sulfated fucan fraction as described in Agricultural and Biological Chemistry, 44 (8): 1965-1966 (1980), which is responsible for anticoagulant activity, and U-fucoidan as described in WO 97/26896, which is responsible for an apoptosis-inducing activity against tumor cells.

The use of the sulfated fucan fraction as an anticoagulant in place of heparin has been examined. However, it is required to obtain a highly pure sulfated fucan in order to use it as a pharmaceutical avoiding side effects due to unexpected activities. Thus, a method therefor has been desired.

Regarding U-fucoidan, it is similarly required to conveniently obtain a highly pure sulfated fucose-containing polysaccharide-U in order to prepare a pharmaceutical utilizing the apoptosis-inducing activity against tumor cells. Thus, a method therefor has been desired.

Generally, enzymatic degradation is the most efficient manner utilized for structural analyses of polysaccharides and production of oligosaccharides. Furthermore, only one polysaccharide can be readily removed from a mixture of polysaccharides which are hardly separated from each other as follows. The polysaccharide to be removed is converted into a smaller molecule using an enzyme that specifically degrades the polysaccharide. The mixture is then subjected to molecular weight fractionation such as ultrafiltration.

It has been reported that abalones, scallops, sea urchins, marine microorganisms and the like produce enzymes that degrade sulfated fucose-containing polysaccharides. However, only a trace amount of such an enzyme is generally contained in an organism. In addition, since such an organism has plural sulfated fucose-containing polysaccharide-degrading enzymes, various purification steps are required for obtaining a single enzyme. For example, the sulfated fucogalactan-degrading enzyme as described in WO 00/50464 was separated using its activity as an index, although it is unknown if it was isolated as a single protein. As described above, it is difficult to purify and collect a large amount of a single naturally occurring sulfated fucogalactan-degrading enzyme. Furthermore, it is necessary to add a sulfated fucogalactan or sulfated fucose-containing polysaccharides including a sulfated fucogalactan to a culture in order to obtain a sulfated fucogalactan-degrading enzyme from a marine microorganism. Thus, there are problems that the cultivation procedure is made complicated and the cost is made high.

There are further problems as follows. If a sufficient amount of a naturally occurring sulfated fucogalactan-degrading enzyme protein cannot be obtained as described above, it is almost impossible to obtain information about the amino acid sequence or the nucleotide sequence for the enzyme. Information about the N-terminal amino acid sequence might not be obtained due to blocking of the enzyme protein at the N-terminus even if a sufficient amount could be obtained.

In addition, there may be unexpected problems as follows. Even if a gene encoding such an enzyme could be obtained, the gene might not be expressed or the expression level might be low due to the incompatibility between the gene and the expression promoter or the host. Alternatively, a recombinant enzyme retaining an enzymatic activity might not be obtained due to formation of inclusion bodies.

OBJECTS OF INVENTION

The main object of the present invention is to provide a gene encoding a polypeptide that has an activity of degrading a sulfated fucogalactan which is useful as a reagent for glycotechnology, for a structural analysis of a sulfated fucose-containing polysaccharide or for preparation of a smaller molecule from the polysaccharide, a method for producing the polypeptide using genetic engineering techniques, and a polypeptide obtainable by the method.

SUMMARY OF INVENTION

The present inventors have intensively carried out researches on a gene from a microorganism producing a sulfated fucogalactan-degrading enzyme in order to reveal an amino acid sequence and a nucleotide sequence for a polypeptide having a sulfated fucogalactan-degrading activity contained in a brown alga. As a result, the present inventors have revealed the existence of at least two genes that encode polypeptides each having an activity of degrading a sulfated fucogalactan derived from a bacterium of the genus *Flavobacterium*, and determined the nucleotide sequences of the genes. The present inventors have also revealed the amino acid sequences of the polypeptides. Furthermore, the present inventors have successfully developed an industrially advantageous method for producing polypeptides each having an activity of degrading a sulfated fucogalactan using the genes. Thus, the present invention has been completed.

The first aspect of the present invention relates to a polypeptide having an activity of degrading a sulfated fucogalactan, which is selected from the group consisting of:

(a) a polypeptide containing the amino acid sequence of SEQ ID NO:28 or 30, or a portion thereof;

(b) a polypeptide having an amino acid sequence in which at least one amino acid residue is deleted, added, inserted or substituted in the amino acid sequence of SEQ ID NO:28 or 30; and (c) a polypeptide having an amino acid sequence that has a homology of at least 30% to the amino acid sequence of SEQ ID NO:28 or 30.

The second aspect of the present invention relates to a nucleic acid encoding a polypeptide having an activity of degrading a sulfated fucogalactan, which is selected from the group consisting of:

(a) a nucleic acid encoding a polypeptide that contains the amino acid sequence of SEQ ID NO:28 or 30, or a portion thereof;

(b) a nucleic acid encoding a polypeptide that has an amino acid sequence in which at least one amino acid residue is deleted, added, inserted or substituted in the amino acid sequence of SEQ ID NO:28 or 30;

(c) a nucleic acid containing a nucleotide sequence of SEQ ID NO:27 or 29;

(d) a nucleic acid consisting of a nucleotide sequence in which at least one nucleotide is deleted, added, inserted or substituted in the nucleotide sequence of SEQ ID NO:27 or 29;

(e) a nucleic acid capable of hybridizing to any one of the nucleic acids of (a) to (d) or a complementary strand thereof under stringent conditions; and (f) a nucleic acid having a nucleotide sequence that has a homology of at least 50% to the nucleotide sequence of SEQ ID NO:27 or 29.

According to the second aspect, a polypeptide having an activity of converting a sulfated fucogalactan into a smaller molecule to release at least one selected from the compounds of the formulas (I), (II), (III) and (IV) is provided:

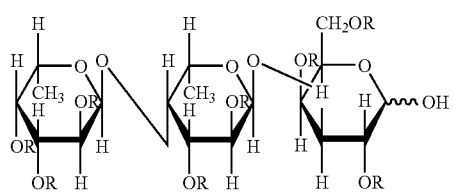

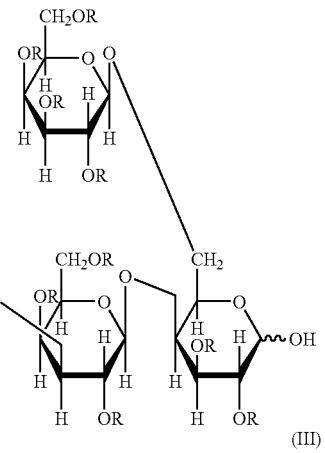

wherein R is H or SO$_3$H.

The third aspect of the present invention relates to a recombinant DNA containing the nucleic acid of the second aspect.

The fourth aspect of the present invention relates to an expression vector for a microorganism, an animal cell or a plant cell as a host cell into which the recombinant DNA of the third aspect is inserted.

The fifth aspect of the present invention relates to a transformant transformed with the recombinant DNA of the third aspect or the expression vector of the fourth aspect.

The sixth aspect of the present invention relates to a method for producing a polypeptide having an activity of degrading a sulfated fucogalactan, the method comprising:
culturing the transformant of the fifth aspect; and
collecting a polypeptide having an activity of degrading a sulfated fucogalactan from the culture.

The seventh aspect of the present invention relates to a polypeptide having an activity of degrading a sulfated fucogalactan which is obtainable by culturing *Escherichia coli* BL21(DE3)/pEA101 (FERM BP-8149) or *Escherichia coli* BL21(DE3)/pEB101 (FERM BP-8150).

The eighth aspect of the present invention relates to a smaller molecule from a sulfated fucogalactan which is obtainable by allowing the polypeptide having an activity of degrading a sulfated fucogalactan of the first or seventh aspect to act on a sulfated fucogalactan.

The ninth aspect of the present invention relates to a method for producing a smaller molecule from a sulfated fucogalactan, the method comprising allowing the polypeptide having an activity of degrading a sulfated fucogalactan of the first or seventh aspect to act on a sulfated fucogalactan.

According to the ninth aspect, a method in which the polypeptide having an activity of degrading a sulfated fucogalactan is allowed to act on a deacetylated sulfated fucogalactan is provided.

The tenth aspect of the present invention relates to a method for screening for a gene encoding a polypeptide having an activity of degrading a sulfated fucogalactan, the method comprising screening, using the gene of the second aspect or a portion thereof as a probe, for a gene encoding a polypeptide having an activity of degrading a sulfated fucogalactan.

The eleventh aspect of the present invention relates to a method for analyzing a structure of a polysaccharide, the method comprising allowing the polypeptide having an activity of degrading a sulfated fucogalactan of the first or seventh aspect to act on a sulfated fucogalactan.

DETAILED DESCRIPTION OF THE INVENTION

The present invention will be explained in detail.

As used herein, a sulfated fucogalactan refers to a sulfated fucose-containing polysaccharide as described in WO 00/50464. The sulfated fucogalactan mainly contains galactose and fucose as constituting saccharides at a molar ratio of 1:1 to 6:1. Examples thereof include a sulfated fucogalactan containing galactose and fucose at a molar ratio of 2:1. The sulfated fucogalactan is a sulfated polysaccharide having an average molecular weight of about 130,000 (molecular weight distribution: about 100,000 to about 200,000) as determined using HPLC gel filtration, for example. The molecular weight, the saccharide composition, the acetyl group content and the sulfate group content of the sulfated fucogalactan may vary depending on the harvest time of the raw material for the sulfated fucogalactan, the method used for drying the raw material and the method used for storing the raw material. In addition, they may vary depending on the heating conditions, pH and the like used for extracting the sulfated fucogalactan. For example, the sulfated fucogalactan may be hydrolyzed with acid. Thus, the molecular weight, the molecular weight distribution, the saccharide composition, the acetyl group content or the sulfate group content of the sulfated fucogalactan as described herein is just an example, and it may be readily changed depending on the conditions used for extracting the sulfated fucogalactan. For example, if a sulfated fucogalactan is prepared using the U-fucoidan-degrading enzyme and the F-fucoidan-degrading enzyme as described herein, a sulfated fucogalactan having the saccharide composition and the molecular weight as described above is obtained. Thus, a sulfated fucogalactan having any molecular weight, molecular weight distribution, saccharide composition, acetyl group content or sulfate group content can be prepared using appropriately selected preparation conditions. For example, about five sulfate group residues are contained in six principal constituting saccharides of the sulfated fucogalactan. Generally, sulfate groups attached to saccharides through ester bonds are chemically unstable and readily cleaved with acid, alkali or heat. The sulfate group content is reduced, for example, by heating under acidic or alkaline conditions. That is, the sulfated fucogalactan can be intentionally desulfated. The amount of sulfate groups to be cleaved can be controlled by appropriately selecting the type and/or the concentration of the acid or the alkali as well as the temperature and/or the time of heating upon the desulfation. Also, acetyl groups attached through ester bonds can be cleaved in a similar manner. Thus, the sulfated fucogalactans according to the present invention include all of those derived from brown algae that have the features as described above or that are converted into smaller molecules by the action of the sulfated fucogalactan-degrading enzyme of the present invention.

The main backbone of the sulfated fucogalactan according to the present invention is represented by general formula (V) below. The sulfated fucogalactans include those of the general formula wherein n is an integer of 1 or more, for example 1 to 1000, preferably 1 to 500.

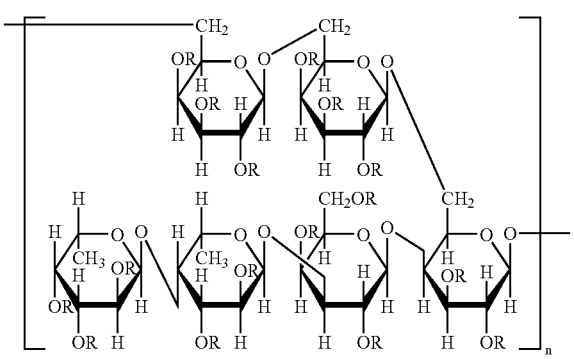

(V)

wherein R is H, $SO_3H$ or $COCH_3$.

Examples of the brown algae from which the sulfated fucogalactans according to the present invention can be prepared include, but are not limited to, *Kjellmaniella crassifolia*, *Undaria pinnatifida*, *Laminaria japonica*, *Eisenia bicyclis*, *Ecklonia cava*, *Ecklonia kurome*, *Lessonia nigrescence*, giant kelp and durvillaea. Although it is not intended to limit the present invention, for example, fucoidans derived from *Kjellmaniella crassifolia* contain U-fucoidan and F-fucoidan as well as G-fucoidan.

Pharmaceutically acceptable salts can be used as the salts of the sulfated fucogalactan of the present invention. Examples of the salts include salts with alkaline metals such as sodium and potassium, alkaline earth metals such as calcium and magnesium and transition metals such as zinc as well as ammonium salts.

As used herein, a smaller molecule from a sulfated fucogalactan refers to an oligosaccharide having sulfated galactose or galactose at its reducing end, which is obtainable by allowing the sulfated fucogalactan-degrading enzyme of the present invention to act on a sulfated fucogalactan.

Hereinafter, the present invention will be described in detail.

(1) Polypeptide Having Activity of Degrading Sulfated Fucogalactan

As used herein, a polypeptide having an activity of degrading a sulfated fucogalactan (also simply referred herein to as a sulfated fucogalactan-degrading enzyme) refers to a polypeptide that acts on a sulfated fucogalactan or a deacetylated sulfated fucogalactan to convert the sulfated fucogalactan into a smaller molecule and generate an oligosaccharide having sulfated galactose or galactose at the reducing end. The endo-type sulfated fucose-containing polysaccharide-degrading enzyme as described in WO 97/26896, which degrades the sulfated fucose-containing polysaccharide-F, does not degrade the sulfated fucogalactan according to the present invention.

The polypeptide having an activity of degrading a sulfated fucogalactan of the present invention is exemplified by a polypeptide having an activity of degrading a sulfated fucogalactan derived from *Flavobactrium* sp. SA-0082 which is isolated and purified according to the present invention. The sulfated fucogalactan-degrading enzyme is an enzyme that degrades β1-6 bonds and β1-4 bonds between D-sulfated galactose or galactose and D-sulfated galactose or galactose in a sulfated fucogalactan in an endo-type manner.

An exemplary strain producing an enzyme that degrades a sulfated fucogalactan according to the present invention is *Flavobacterium* sp. SA-0082 which is described in WO 97/26896. *Flavobacterium* sp. SA-0082 is deposited on Mar. 29, 1995 at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM P-14872, and deposited at International Patent Organism Depositary, National Institute of Advanced Industrial Science and Technology under accession number FERM BP-5402 (date of request for transmission to international depositary authority: Feb. 15, 1996).

The polypeptide having an activity of degrading a sulfated fucogalactan of the present invention is exemplified by a polypeptide derived from a bacterium of the genus *Flavobacterium* which has an activity of degrading a sulfated fucogalactan as follows:

(I) acting on a sulfated fucogalactan containing galactose and fucose as constituting saccharides at a molar ratio of 1:1 to 6:1 or a salt thereof to convert the sulfated fucogalactan into a smaller molecule and generate an oligosaccharide having sulfated galactose or galactose at its reducing end;

(II) having an optimal pH of about 7 to 9; and (III) having an optimal temperature of about 25 to 45° C.

Polypeptides having an activity of degrading a sulfated fucogalactan according to the present invention include not only a naturally occurring sulfated fucogalactan-degrading enzyme but also a polypeptide having a modified amino acid sequence by deletion, substitution, insertion or addition of an amino acid in a naturally occurring amino acid sequence and having an activity of degrading a sulfated fucogalactan. Examples of the naturally occurring sulfated fucogalactan-degrading enzymes include, but are not limited to, ones derived from bacteria of the genus *Flavobacterium*, as well as ones derived from microorganisms such as other bacteria, yeasts, filamentous fungi, ascomycetes and basidomycetes, and plants and animals as long as they have amino acid or nucleotide sequence homologies to those of the present invention.

The polypeptides of the present invention include a polypeptide having an amino acid sequence in which at least one amino acid residue is deleted, added, inserted or substituted in the amino acid sequence of SEQ ID NO:28 or 30 and having a functionally equivalent activity as long as it exhibits an activity of degrading a sulfated fucogalactan.

As used herein, a polypeptide having a functionally equivalent activity refers to the following.

A mutation such as deletion, addition, insertion or substitution of an amino acid residue in an amino acid sequence may be generated in a naturally occurring protein. Such mutation may be generated due to a polymorphism or a mutation of the gene encoding the protein, or due to a modification reaction in vivo or during purification after synthesis of the protein. It is known that such a mutated protein may nevertheless exhibit a physiological or biological activity substantially equivalent to that of a protein without a mutation. A polypeptide having a functionally equivalent activity refers to one for which no significant difference in the function is recognized in spite of the difference in the structure.

This is applicable to a protein in which such a mutation is artificially introduced into an amino acid sequence of a protein. In this case, it is possible to produce more various mutations. Such a mutant is construed as a polypeptide having a functionally equivalent activity as long as it exhibits a physiological activity substantially equivalent to one without a mutation.

For example, it is said that a methionine residue at the N-terminus of a protein expressed in *Escherichia coli* may be removed by the action of methionine aminopeptidase in many cases, and both one having the methionine residue and one lacking the methionine residue may be generated depending on the type of the protein. In many cases, the presence of the methionine residue does not influence the activity of the protein. Furthermore, it is known that a polypeptide in which a cysteine residue in the amino acid sequence of human interleukin-2 (IL-2) is replaced by a serine residue retains the interleukin-2 activity (Science, 224:1431 (1984)). Thus, activities of interest may be exhibited in spite of amino acid substitution.

Polypeptides having a functionally equivalent activity are homologous to each other in many cases. Thus, a polypeptide that is homologous to the polypeptide of the present invention and has an activity of degrading a sulfated fucogalactan is encompassed by the present invention.

Homology can be determined, for example, using a computer program DNASIS-Mac (Takara Shuzo), a computer algorithm FASTA (version 3.0; Pearson, W. R. et al., Pro. Natl. Acad. Sci., 85:2444-2448, 188), or a computer algorithm BLAST (version 2.0; Altschul et al., Nucleic Acids Res., 25:3389-3402, 1997).

A polypeptide having an amino acid sequence having homology of 30% or more, preferably 40% or more, more preferably 50% or more, most preferably 59% or more to the amino acid sequence disclosed herein (SEQ ID NO:28 or 30) is encompassed by the present invention as long as it has an activity of degrading a sulfated fucogalactan.

Only a sulfated fucogalactan contained in any fraction containing sulfated fucose-containing polysaccharides can be converted into a smaller molecule by using the polypeptide having an activity of degrading a sulfated fucogalactan of the present invention. Thus, a sulfated fucogalactan can be selectively removed by using the polypeptide in combination with molecular weight fractionation. For example, it has been reported that fractions containing sulfated fucans have various biological activities such as an anticoagulant activity, an activity of suppressing cancer metastasis and an activity of suppressing viral infection. Fractions containing sulfated fucans obtained from brown algae contain sulfated fucans and other polysaccharides. A sulfated fucogalactan can be removed from a fraction containing a sulfated fucan by utilizing the sulfated fucogalactan-degrading enzyme of the present invention. Consequently, a highly pure sulfated fucan can be obtained.

Furthermore, it has been reported that, for example, a sulfated fucoglucuronomannan has an apoptosis-inducing activity against tumor cells. A sulfated fucogalactan contaminating in a sulfated fucoglucuronomannan obtained from a brown alga can be readily removed by utilizing the sulfated fucogalactan-degrading enzyme of the present invention. Consequently, a highly pure sulfated fucoglucuronomannan can be conveniently obtained.

For example, a solution of a sulfated fucogalactan-containing material in an aqueous solvent is prepared a method for removing a sulfated fucogalactan. The sulfated fucogalactan-containing material may be dissolved according to a conventional method. The sulfated fucogalactan-containing material may be dissolved in the solution at the maximal concentration. However, the concentration is usually selected taking its operationality and the titer of the enzyme to be used into consideration. The solvent used for dissolving a sulfated fucogalactan may be selected from water, buffers and the like depending on the object. Usually, the preferable pH of the solution is nearly neutral. The sulfated fucogalactan-degrading enzyme of the present invention or a substance onto which the enzyme has been immobilized, or both, is then added to and reacted with the solution of the sulfated fucogalactan-containing material to convert the sulfated fucogalactan into a smaller molecule. The enzymatic reaction is usually carried out at about 30° C. The amount of the enzyme, the reaction time and the like may be suitably adjusted depending on the ability of molecular weight fractionation in the subsequent step. A product of interest from which the smaller molecule from a sulfated fucogalactan have been removed can be readily prepared by subjecting the resulting mixture to molecular weight fractionation. Conventional means for molecular weight fractionation such as gel filtration and ultrafiltration utilizing a molecular weight fractionation membrane can be applied.

Sine the sulfated fucogalactan-degrading enzyme of the present invention acts on sulfated fucogalactans, it can be used for structural analyses of sulfated fucogalactans.

Furthermore, a sulfated fucogalactan component can be selectively removed from a mixture of sulfated fucose-containing polysaccharides including a sulfated fucogalactan by using the sulfated fucogalactan-degrading enzyme of the present invention. For example, a highly pure sulfated fucan or sulfated fucoglucuronomannan from which a sulfated fucogalactan component has been removed can be preferably used as a raw material for a pharmaceutical.

(2) Gene Encoding Polypeptide Having Activity of Degrading Sulfated Fucogalactan Genes encoding polypeptides having a functionally equivalent activity are homologous to each other in many cases. Thus, a gene that is capable of hybridizing to the gene used according to the present invention under stringent conditions and encodes a polypeptide having an activity of degrading a sulfated fucogalactan is encompassed by the present invention.

Homology between nucleotide sequences can be determined using a computer program DNASIS-Mac, or a computer algorithm FASTA (version 3.0) or BLAST (version 2.0).

The nucleic acid of the present invention is a nucleic acid that encodes the polypeptide of the present invention. Specifically, the nucleic acids of the present invention include (1) a nucleic acid encoding a polypeptide that contains the amino acid sequence of SEQ ID NO:28 or 30, or has an amino acid sequence in which at least one amino acid residue is deleted, added, inserted or substituted in the amino acid sequence of SEQ ID NO:28 or 30 and exhibits an activity of degrading a sulfated fucogalactan; (2) a nucleic acid containing a nucleotide sequence of SEQ ID NO:27 or 29; or (3) a nucleic acid that is capable of hybridizing to the nucleic acid of (1) or (2) under stringent conditions, or has a nucleotide sequence that has a homology of 50% or more, preferably 60% or more, more preferably 65% or more, most preferably 69% or more to the nucleotide sequence of (1) or (2), and encodes a polypeptide that exhibits an activity of degrading a sulfated fucogalactan.

As used herein, a nucleic acid means a single-stranded or double-stranded DNA or RNA. If the nucleic acid of (2) above is an RNA, it is represented by a nucleotide sequence in which T is replaced by U in the nucleotide sequence of SEQ ID NO:27, for example.

For example, the nucleic acid of the present invention can be obtained as follows.

The nucleic acid of (2) above containing the nucleotide sequence of SEQ ID NO:27 or 29 can be isolated as follows. A genomic DNA is prepared according to a conventional method from a microorganism, a plant, an animal or the like that produces a polypeptide having an activity of degrading a sulfated fucogalactan. The genomic DNA is used to construct a DNA library. The nucleic acid can be isolated from the DNA library. Also, the nucleic acid can be obtained by amplifying a nucleic acid containing a nucleotide sequence of SEQ ID NO:27 or 29 in a polymerase chain reaction (PCR) using the genomic DNA as a template.

Furthermore, a nucleic acid encoding a polypeptide having an activity of degrading a sulfated fucogalactan similar to that of the polypeptide of the present invention can be obtained on the basis of the nucleotide sequence of the nucleic acid encoding the polypeptide of the present invention which is provided by the present invention (e.g., the nucleotide sequence of SEQ ID NO:27 or 29). Specifically, a DNA encoding a polypeptide having an activity of degrading a sulfated fucogalactan can be screened, using the nucleic acid encoding the polypeptide of the present invention or a portion of the nucleotide sequence as a probe for hybridization, from DNAs extracted from cells, PCR products obtained using the DNAs as templates or the like. Alternatively, a DNA encoding a polypeptide having an activity of degrading a sulfated fucogalactan can be amplified using a gene amplification method such as a PCR using a primer designed based on the above-mentioned nucleotide sequence. Additionally, a DNA encoding a polypeptide having an activity of degrading a sulfated fucogalactan can be chemically synthesized. The nucleic acid of (1) or (3) above can be obtained according to such a method.

A nucleic acid fragment containing only a portion of the nucleic acid of interest may be obtained according to the above-mentioned method. In this case, the entire nucleic acid of interest can be obtained as follows. The nucleotide sequence of the obtained nucleic acid fragment is examined to confirm that the fragment is a portion of the nucleic acid of interest. Hybridization is carried out using the nucleic acid fragment or a portion thereof as a probe. Alternatively, a PCR is carried out using a primer synthesized based on the nucleotide sequence of the nucleic acid fragment.

If the nucleotide sequence is known, the probe or the primer can be designed to have an optimal sequence for the object, the condition or the environment to be used using a computer program such as Oligo™ Primer Analysis Software (Takara Shuzo).

"Hybridize under stringent conditions" refers to being capable of hybridizing under conditions as described in the Sambrook, Fritsch and Maniatis (eds.), Molecular Cloning: A Laboratory Manual 2nd ed., Cold Spring Harbor Laboratory (1989), for example, under the following conditions. Briefly, a membrane onto which a nucleic acid is immobilized is incubated with a probe in 6×SSC (1×SSC: 0.15 M NaCl, 0.015 M sodium citrate, pH 7.0) containing 0.5% SDS, 0.1% bovine serum albumin (BSA), 0.1% polyvinylpyrrolidone, 0.1% Ficoll 400 and 0.01% denatured salmon sperm nucleic acid at 50° C. for 12 to 20 hours or alternatively containing 5× Denhardt's reagent, 0.5% SDS, 100 µg/ml denatured, fragmented salmon sperm DNA at 68° C. for 12-20 hours. After incubation, the membrane is washed in 2×SSC containing 0.5% SDS at 37° C. (alternatively in 2×SSC, 0.1% SDS at room temperature) while changing the SSC concentration down to 0.1×SSC and the temperature up to 68° C. until the signal from the immobilized nucleic acid can be distinguished from background, and the probe is then detected. The activity of the protein encoded by the thus obtained novel nucleic acid can be determined according to the method as described above, thereby confirming whether or not the nucleic acid is the desired one.

If an oligonucleotide probe is used, "stringent conditions" refer to, for example, incubation at a temperature of [Tm−25° C.] overnight in a solution containing 6×SSC, 0.5% SDS, 5× Denhardt's and 0.01% denatured salmon sperm nucleic acid, although it is not intended to limit the present invention.

Tm of an oligonucleotide probe or primer can be determined, for example, according to the following equation:

$$Tm=81.5-16.6(\log_{10}[Na^{+1}]+0.41(\% \ G+C)-(600/N)$$

wherein N is the chain length of the oligonucleotide probe or primer; % G+C is the content of guanine and cytosine residues in the oligonucleotide probe or primer.

If the chain length of the oligonucleotide probe or primer is shorter than 18 nucleotides, Tm can be estimated, for example, as the sum of the product of the number of A+T (adenine and thymine) residues multiplied by 2(° C.) and the product of the number of G+C residues multiplied by 4(° C.):

$$[(A+T)\times 2+(G+C)\times 4].$$

As described above, a nucleic acid that is capable of hybridizing to the nucleic acid encoding the polypeptide of the present invention under stringent conditions is encompassed by the present invention as long as it encodes a polypeptide having an activity of degrading a sulfated fucogalactan even if it does not have the same nucleotide sequence as that disclosed herein.

Once a vector containing the DNA fragment of interest is selected, the nucleotide sequence of the DNA fragment of interest inserted into the vector can be determined according to a conventional method such as the dideoxy method (Proc. Nat. Acad. Sci, U.S.A., 74:5463 (1977)). It is possible to obtain information about the structure of the gene in the DNA fragment and the amino acid sequence of the polypeptide encoded by the gene. The information can be obtained by comparing the determined nucleotide sequence with the analyzed N-terminus, the partial amino acid sequence(s), the molecular weight or the like of the sulfated fucogalactan-degrading enzyme.

The PCR method can be used to obtain a gene encoding a polypeptide that has an activity of degrading a sulfated fucogalactan using an oligonucleotide prepared on the basis of the partial amino acid sequence of the sulfated fucogalactan-degrading enzyme. In particular, a PCR method using a cassette DNA (Takara Shuzo) can be used to obtain, in a short time on the basis of little information about the amino acid sequence, a fragment of the gene of interest which can be used for hybridization.

For example, a genomic DNA extracted from cultured Flavobacterium sp. SA-0082 cells according to a conventional method is digested with an appropriate restriction enzyme and ligated with a synthetic DNA having a known sequence (a cassette DNA). A DNA fragment of interest can be amplified by carrying out a PCR using the ligation mixture as a template as well as a gene-specific oligonucleotide primer designed on the basis of the above-mentioned information about the partial amino acid sequence and an oligonucleotide primer complementary to the cassette DNA (a cassette primer). For example, one available from Takara Shuzo can be used as the cassette DNA or the cassette primer. The cassette DNA preferably contains sequences corresponding to two cassette primers. It is effective to carry out a first PCR using a primer corresponding to a sequence distal to the restriction enzyme site subjected to ligation, and then carry out a second PCR using a portion of the reaction mixture of the first PCR as a template and a primer corresponding to an inner sequence. Also regarding the gene-specific oligonucleotide primer, specificity for the gene and possibility of specific amplification of the DNA fragment of interest may be increased by designing and synthesizing two adjacent gene-specific oligonucleotide primers and using the upstream primer for a first PCR and the downstream primer for a second PCR.

A site for the restriction enzyme used for ligating the cassette DNA is not necessarily located at a distance suitable for a PCR amplification reaction from the region encoding the partial amino acid sequence because the nucleotide sequence of the gene of interest is unknown. Therefore, it is necessary to examine the use of cassette DNAs for a variety of restriction enzyme sites. In addition, a PCR may be carried out under commonly used conditions such as those described in Erlich, H. A. (ed.), PCR Technology, Stockton Press, 1989. However, it is necessary to select optimal conditions for the length of the synthetic oligonucleotide to be used or the complementarity to the gene encoding a polypeptide having an activity of degrading a sulfated fucogalactan in order to minimized nonspecifically amplified bands. The selection may be achieved by examining the annealing temperature, the cycle number, the magnesium concentration, the heat-resistant polymerase concentration and the like.

The PCR reaction mixture is subjected to electrophoresis on agarose gel or the like to confirm the amplified DNA fragment. The nucleotide sequence of the fragment can be analyzed, for example according to the dideoxy method, after extracting and purifying it according to a conventional method and inserting into a conventional cloning vector (e.g., pUC18 or pUC19). Alternatively, the nucleotide sequence of the recovered amplified DNA fragment may be directly analyzed using the cassette primer used for the PCR. If the analysis reveals obtainment of one encoding, in addition to the primer sequence, the previously determined partial amino acid sequence of the sulfated fucogalactan-degrading enzyme, then a fragment of a gene encoding the enzyme or a gene homologous thereto is obtained.

If the DNA fragment obtained by the Southern hybridization method or the PCR method as described above is a part of a gene encoding the enzyme of interest, a DNA fragment containing the entire gene encoding the enzyme of interest can be obtained by screening a genomic library by hybridization using the DNA fragment as a probe, or by carrying out a PCR using an oligonucleotide prepared based on the nucleotide sequence of the DNA fragment as a primer. The genomic DNA from Flavobacterium sp. SA-0082 is analyzed by the Southern hybridization method using the thus obtained sulfated fucogalactan-degrading enzyme gene or a portion thereof as a probe. Then, information about the size of a restriction fragment of the Flavobacterium sp. SA-0082 genomic DNA that contains a gene encoding the polypeptide having an activity of degrading a sulfated fucogalactan can be obtained based on the position of the detected band. Furthermore, the number of genes encoding polypeptides having activities of degrading a sulfated fucogalactan or genes having complementarity thereto can be estimated based on the number of the detected bands. Such DNA fragments containing the genes can be isolated according to the method as described above.

It is possible to confirm whether or not the thus obtained DNA fragment contains a gene encoding the enzyme of interest by constructing an expression vector containing the finally isolated DNA fragment, transforming a host with the vector, culturing the transformant and determining the activity of degrading a sulfated fucogalactan of the expressed polypeptide.

(3) Transformant Containing Gene Encoding Polypeptide Having Activity of Degrading Sulfated Fucogalactan A recombinant DNA can be constructed by ligating the nucleic acid encoding the polypeptide of the present invention (e.g., a nucleic acid having the nucleotide sequence of SEQ ID NO:27 or 29) to an appropriate vector. There is no specific limitation concerning the vector to be used for the construction of the recombinant DNA. For example, plasmid vectors, phage vectors and virus vectors can be used. A suitable vector for the intended use of the recombinant DNA is selected.

Furthermore, a transformant can be produced by introducing the recombinant DNA into an appropriate host. There is no specific limitation concerning the host to be used for the production of the transformant. Microorganisms such as bacteria, yeasts and filamentous fungi as well as cultured cells from animals, plants, insects and like can be used. The polypeptide of the present invention can be produced in large quantities by culturing the transformant to produce the polypeptide of the present invention in the culture.

The polypeptide of the present invention can be obtained from a transformant transformed with a recombinant DNA containing the nucleic acid of the present invention (e.g., a nucleic acid having a nucleotide sequence of SEQ ID NO:27 or 29). Polypeptides having the amino acid sequences of SEQ ID NOS:28 and 30 are generated from nucleic acids having the nucleotide sequences of SEQ ID NOS:27 and 29, respectively.

The present invention will be more specifically described below with respect to *Flavobactrium* sp. SA-0082 as an example.

The microorganism indicated as *Flavobactrium* sp. SA-0082 is deposited under Budapest Treaty under accession number FERM BP-5402 at International Patent Organism Depositary, National Institute of Advanced Industrial Science and Technology.

For example, the hybridization method, the PCR method or a combination thereof can be utilized for obtaining a gene encoding a polypeptide having an activity of degrading a sulfated fucogalactan produced by *Flavobactrium* sp. SA-0082. A probe capable of hybridizing to the gene or a primer that can be used to amplify the gene or a portion thereof by the PCR method is necessary for such a method. However, since the amino acid sequence of a polypeptide having an activity of degrading a sulfated fucogalactan produced by this strain or the structure of the gene for the polypeptide is not known at all, it is impossible to prepare a synthetic oligonucleotide that can be utilized as a probe or a primer. So, a partial amino acid sequence of a sulfated fucogalactan-degrading enzyme produced by the microorganism is first determined to examine preparation of a synthetic oligonucleotide that can be utilized as a probe or a primer.

*Flavobactrium* sp. SA-0082 is cultured, and a sulfated fucogalactan-degrading enzyme produced by the microorganism is isolated and purified from the culture. Information on a partial amino acid sequence of the purified sulfated fucogalactan-degrading enzyme is then obtained. A partial amino acid sequence is determined, for example, by directly subjecting the sulfated fucogalactan-degrading enzyme to an amino acid sequence analysis by Edman degradation according to a conventional method to determine the N-terminal amino acid sequence of the sulfated fucogalactan-degrading enzyme. For example, Protein Sequencer 476A (Applied Biosystems) can be used for the analysis. Since the N-terminus of the polypeptide of the enzyme purified from *Flavobactrium* sp. SA-0082 was blocked, no information about the N-terminal amino acid sequence was available. In such a case, the purified sulfated fucogalactan-degrading enzyme is subjected to limited proteolysis by allowing a highly specific proteolytic enzyme (e.g., Achromobacter protease I, N-tosyl-L-phenylalanyl chloromethyl ketone (TPCK)-trypsin) to act thereon. The resulting peptide fragments are separated and purified using reverse phase HPLC. The, a lot of information on amino acid sequences can be obtained by subjecting the purified peptide fragments to amino acid analyses.

An oligonucleotide having a degenerated nucleotide sequence is designed and synthesized on the basis of the selected information about the partial amino acid sequence specific for the sulfated fucogalactan-degrading enzyme obtained as described above. It is necessary to synthesize a long oligonucleotide with low degeneracy, i.e., an oligonucleotide highly specific for the gene encoding the polypeptide having an activity of degrading a sulfated fucogalactan. The design of the oligonucleotide is an important factor in cloning of the gene encoding the polypeptide having an activity of degrading a sulfated fucogalactan.

Next, it is necessary to examine conditions used for specific hybridization between the synthetic oligonucleotide and the gene encoding the polypeptide having an activity of degrading a sulfated fucogalactan using the Southern hybridization method.

For example, a genomic DNA from *Flavobactrium* sp. SA-0082 is completely digested with an appropriate restriction enzyme, separated by agarose gel electrophoresis, and blotted onto a nylon membrane or the like according to a conventional method. Hybridization is carried out as follows. For example, the nylon membrane is subjected to blocking by incubating it at 65° C. for several hours in a prehybridization solution containing 6×SSC (1×SSC: a solution containing 8.77 g of sodium chloride and 4.41 g of sodium citrate in 1 liter of water), 1% sodium lauryl sulfate (SDS), 100 μg/ml of salmon sperm DNA and 5× Denhardt's (containing bovine serum albumin, polyvinylpyrrolidone and Ficoll at concentrations of 0.1%). Then, it is incubated at 42° C. overnight after adding thereto the synthetic oligonucleotide (for example, labeled with $^{32}$p). The nylon membrane is washed at 42° C. for 30 minutes in 1×SSC containing 0.1% SDS, and then a DNA fragment hybridized with the synthetic oligonucleotide probe is detected by autoradiography. It is effective to examine the incubation temperatures, the salt concentration of the washing solution and the like to select the optimal conditions depending on the complementarity with the gene encoding the polypeptide having an activity of degrading a sulfated fucogalactan or the length of the synthetic oligonucleotide used.

The detected DNA fragment containing the gene encoding the polypeptide having an activity of degrading a sulfated fucogalactan may be obtained as follows. DNA fragments corresponding to the position of the detected band are extracted and purified from the gel, and incorporated into a vector for a conventional host-vector system to prepare a library. A clone containing the DNA fragment of interest is then screened and isolated by carrying out colony or plaque hybridization under the conditions similar to those used for the Southern hybridization method. Alternatively, a clone containing the DNA fragment of interest may be directly screened and isolated similarly by the hybridization method from a library prepared by incorporating a genomic DNA from *Flavobactrium* sp. SA-0082 digested with an appropriate restriction enzyme into a vector for a conventional host-vector system.

A recombinant DNA can be constructed by ligating the thus obtained nucleic acid with an appropriate vector. There is no specific limitation concerning the vector to be used for construction of the recombinant DNA. For example, plasmid vectors, phage vectors and virus vectors can be used. A suitable vector for the intended use of the recombinant DNA is selected. Furthermore, the transformant of the present invention can be produced by introducing the recombinant DNA into an appropriate host. There is no specific limitation concerning the host to be used for the production of the transformant. Microorganisms such as bacteria, yeasts and filamentous fungi as well as cultured cells from animals, plants, insects and like can be used.

(4) Method for Producing the Polypeptide of the Present Invention

A known host-vector system can be used. For example, a plasmid vector (e.g., pUC18 or pUC19) or a phage vector (e.g., lambda phage) for *Escherichia coli* as a host may be used, although it is not intended to limit the present invention. A commonly used type or handling method of such a host-vector system (for example, as described in J. Sambrook et al., Molecular Cloning, A Laboratory Manual, Second Edition, Cold Spring Harbor Laboratory, 1989) may be used.

When a protein is produced using genetic engineering techniques, it is often expressed as a fusion protein. For example, an N-terminal peptide chain derived from another protein may be added to the N-terminus of the protein of interest in order to increase the expression level of the protein of interest. Alternatively, an appropriate peptide chain may be added to the N-terminus or the C-terminus of the protein of interest in order to facilitate the purification of the expressed protein of interest by using a carrier having affinity for the added peptide chain.

In addition, the protein of interest may be expressed by incorporating, into an expressed vector, a gene that encodes the protein from which several tens of amino acids at the N- or C-terminus of the protein of interest are deleted.

In many cases, a polypeptide may have an activity functionally equivalent to that of the protein of interest even if one or more amino acid residue is deleted, added, inserted and/or substituted in the amino acid sequence of the protein of interest. Such a polypeptide or a gene encoding such a polypeptide is encompassed by the present invention whether it is a naturally occurring isolate or an artificially produced one.

It is generally known that one to six codon(s) (a combination of three bases), which defines an amino acid in a gene, is assigned for each amino acid. Thus, many genes can encode one specific amino acid sequence although it depends on the amino acid sequence. Genes are not necessarily stable in the nature. Generation of a mutation in a nucleic acid is not unusual. A mutation generated in a gene may not alter the encoded amino acid sequence (called a silent mutation). In this case, it can be said that a different gene encoding the same amino acid sequence is generated. Thus, it cannot be denied that various genes encoding the same amino acid sequence can be generated in the course of passage of an organism containing an isolated gene encoding one specific amino acid sequence. Furthermore, it is not difficult to artificially produce various genes encoding the same amino acid sequence if one uses various genetic engineering techniques.

For example, if a codon used in an original gene encoding a protein of interest is one whose codon usage is low in the host to be used for producing the protein using genetic engineering techniques, the expression level of the protein may be low. In this case, the codon is artificially converted into one frequently used in the host without altering the encoded amino acid sequence aiming at elevating the expression level of the protein of interest. As described above, various genes encoding one specific amino acid sequence can be artificially produced, of course. Thus, such an artificially produced different polynucleotide is encompassed by the present invention as long as it encodes the amino acid sequence disclosed herein. It is known that some polypeptides have peptide regions that are not indispensable to their activities. For example, the regions are exemplified by signal peptides in extracellularly secreted polypeptides and prosequences or preprosequences in precursors of proteases. Most of such regions are removed after translation or after conversion into active polypeptides. Although such a polypeptide has a different primary structure, it finally exhibits an equivalent function. The signal peptide, the prosequence or the preprosequence may inhibit the expression as an active peptide. In this case, the yield of the active peptide may be increased by deleting several amino acid residues to several tens of amino acid residues from the N-terminus of the polypeptide.

The polypeptide of the present invention may be purified from a culture obtained by culturing a transformant into which the plasmid of the present invention, pEA101 or pEB101, is introduced.

There is no specific limitation concerning the host to be transformed. Examples of the hosts include those conventionally used in a field of recombinant DNA including *Escherichia coli*, *Bacillus subtilis*, yeasts, filamentous fungi, plants, animals, plant cultured cells and animal cultured cells.

For example, the polypeptide of the present invention can be expressed in cultured cells as follows. *Escherichia coli* cells harboring a plasmid in which the nucleic acid of the present invention is linked downstream from the lac promoter of the T7 phage promoter are cultured under conventional culture conditions, for example, in LB medium (10 g/l Tryptone, 5 g/l yeast extract, 5 g/l NaCl, pH 7.2) containing 100 μg/ml of ampicillin at 37° C. until logarithmic growth phase. Then, isopropyl-β-D-thiogalactopyranoside is added thereto at a final concentration of 1 mM, and the cells are further cultured at 37° C. In addition, a polypeptide having deletion at the N-terminus of the peptide may be expressed. For example, the expression levels of the peptides of the present invention, sfgA and sfgB, can be increased by deleting 23 and 30 amino acid residues from the N-termini in the full-length amino acid sequences, respectively.

Cells collected by centrifugation after cultivation are disrupted by sonication, and a supernatant collected by centrifugation is used as a cell-free extract. This cell-free extract exhibits an activity of degrading a sulfated fucogalactan. The polypeptide of the present invention can be purified from the cell-free extract by using known methods such as ion exchange chromatography, gel filtration, hydrophobic chromatography and ammonium sulfate precipitation. Naturally, a partially purified product obtained during the above-mentioned purification process also exhibits an activity of degrading a sulfated fucogalactan.

(5) Method for Screening Gene Encoding Polypeptide Having Activity of Degrading Sulfated Fucogalactan For example, the following method can be applied for obtaining, by hybridization using the nucleotide sequence of the gene of the present invention, a gene encoding a polypeptide that has an activity of degrading a sulfated fucogalactan or a functionally equivalent activity.

Chromosomal DNA obtained from a gene source of interest or cDNA prepared from mRNA using a reverse transcriptase is ligated with a plasmid or phage vector according to a conventional method. The ligation mixture is introduced into a host to prepare a library. The library is cultured on plates, and the grown colonies or plaques are transferred to nitrocellulose or nylon membranes. The DNAs are immobilized to the membranes by denaturation. The membranes are incubated in a solution containing a probe (for example, labeled with $^{32}P$) to form a hybrid between DNA on the membranes and the probe. A nucleotide sequence encoding a sequence containing an amino acid sequence of SEQ ID NO:28 or 30 or a portion thereof (e.g., the nucleotide sequence of SEQ ID NO:27 or 29 or a portion thereof) may be used as a probe. For example, the membranes having the immobilized DNAs are subjected to hybridization with a probe at 65° C. for 20 hours in a solution containing 6×SSC, 1% SDS, 100 µg/ml of salmon sperm DNA and 5× Denhardt's. After hybridization, nonspecifically adsorbed probe is washed away, and a clone that has formed a hybrid with the probe is identified by autoradiography or the like. This procedure is repeated until a single hybridizing clone is obtained. A gene encoding the polypeptide of interest is inserted in the thus obtained clone.

The nucleotide sequence of the gene is determined, for example as described below, to confirm if the gene encodes a polypeptide having an activity of degrading a sulfated fucogalactan or a functionally equivalent activity of interest. If the transformant is an *Escherichia coli* cell transformed with a plasmid, the nucleotide sequence is determined as follows. The transformant is cultured in a test tube or the like, and the plasmid is extracted according to a conventional method. The plasmid is cleaved with a restriction enzyme (or restriction enzymes) to obtain the inserted fragment. The fragment is subcloned into an M13 phage vector or the like. Then, the nucleotide sequence is determined according to the dideoxy method. The nucleotide sequence can be determined using basically similar steps if a phage vector is used for the recombinant. The basic experimental methods from cultivation to nucleotide sequence determination are described, for example, in J. Sambrook et al., Molecular Cloning, A Laboratory Manual, Second Edition, Cold Spring Harbor Laboratory 1989.

In order to confirm whether or not the gene encodes the polypeptide having an activity of degrading a sulfated fucogalactan or a functionally equivalent activity of interest, the determined nucleotide sequence or the encoded amino acid sequence is compared with the nucleotide sequence of SEQ ID NO:27 or 29 or the amino acid sequence of SEQ ID NO:28 or 30.

If the obtained gene does not contain the entire region that encodes the polypeptide having an activity of degrading a sulfated fucogalactan or a functionally equivalent activity, the nucleotide sequence of the entire coding region that hybridizes to the gene of the present invention can be determined by amplifying the missing region by a PCR using a synthetic DNA primer prepared based on the obtained gene, or by further screening a DNA library or a cDNA library using the gene fragment as a probe.

Alternatively, a primer for PCR can be designed based on the nucleotide sequence of the gene of the present invention. By carrying out a PCR using the primer, a gene fragment highly homologous to the gene of the present invention can be detected, or the entire gene can be obtained.

The gene is expressed, and the activity of degrading a sulfated fucogalactan of the gene product is measured to determine the function of the gene.

As described above, the present invention provides a primary structure of a polypeptide having an activity of degrading a sulfated fucogalactan and a structure of a gene for the polypeptide. Furthermore, it is now possible to produce a polypeptide having an activity of degrading a sulfated fucogalactan or a functionally equivalent activity using genetic engineering techniques.

By using the production method using genetic engineering techniques of the present invention, it is possible to obtain a highly pure polypeptide having an activity of degrading s sulfated fucogalactan or a functionally equivalent activity at low cost.

According to a method in which a sulfated fucogalactan-degrading enzyme is produced by culturing a bacterium of the genus *Flavobacterium* producing the sulfated fucogalactan-degrading enzyme, proteases and other polysaccharide-degrading enzymes are produced at the same time. Therefore, it is necessary to separate and purify the sulfated fucogalactan-degrading enzyme of interest from such very troublesome enzymes in order to isolate the enzyme of interest. It is now possible to provide a highly pure polypeptide having an activity of degrading a sulfated fucogalactan at low cost according to the present invention.

For example, the activity of degrading a sulfated fucogalactan of the polypeptide encoded by the nucleotide sequence according to the present invention can be confirmed by analyzing, using HPLC, degradation products obtained by allowing the polypeptide to act on a sulfated fucogalactan to determine the degree of conversion into a smaller molecule, or by measuring generated reducing ends according to a conventional method.

(6) Method for Producing Smaller Molecule from Sulfated Fucogalactan and Effect of Deacetylation in the Production Method The smaller molecule from a sulfated fucogalactan of the present invention or a salt thereof can be prepared by allowing the sulfated fucogalactan-degrading enzyme of the present invention to act on a sulfated fucogalactan or a sulfated fucogalactan-containing material. For example, a partially purified product from a sulfated fucogalactan, a fraction of sulfated fucose-containing polysaccharides derived from a brown alga, a product obtained by extracting a brown alga with an aqueous solvent, or a brown alga itself can be preferably used as the sulfated fucogalactan-containing material.

Examples of the smaller molecules obtained by allowing a polypeptide having an activity of degrading a sulfated fucogalactan encoded by the gene of the present invention to act on a sulfated fucogalactan include, but are not limited to, disaccharide to hexasaccharides. The positions of substitution with sulfate groups in the smaller molecules may vary depending on the preparation method. All of the smaller molecules obtained by the action of the sulfated fucogalactan-degrading enzyme of the present invention are included in the smaller molecules of the present invention. For example, the chemical structures of the smaller molecules are represented by general formulas (I) to (IV) below. Among these, general formula (III) is supposed to be the constituting unit of the sulfated fucogalactan.

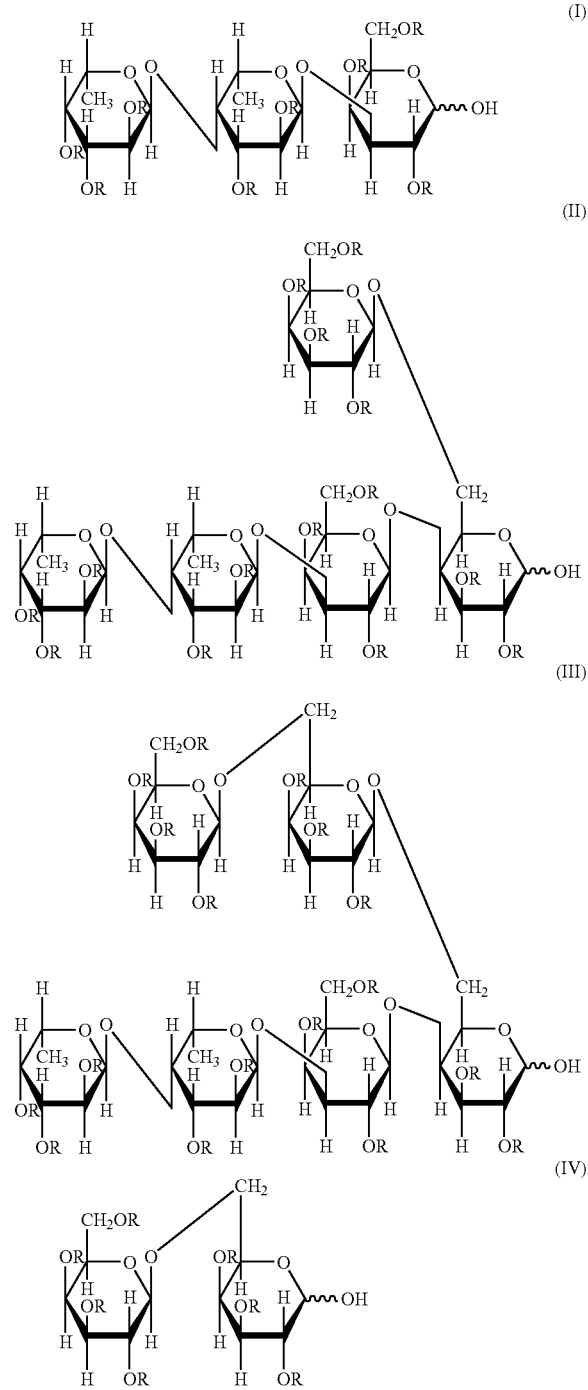

wherein R is H or SO$_3$H.

The smaller molecules of the present invention have sulfate groups within the molecules, which groups react with various bases to form salts. The smaller molecule from a sulfated fucogalactan of the present invention is stable when it is in a form of salt. It is usually provided in a form of sodium and/or potassium and/or calcium salt. The smaller molecule from a sulfated fucogalactan in a free form can be derived from a salt thereof by utilizing cation-exchange resin such as Dowex 50W (Dow Chemical). Optionally, it can be further subjected to conventional salt-exchange to convert it into any one of various salts of interest.

The smaller molecule from a sulfated fucogalactan of the present invention or a salt thereof can be used as an antigen. An antibody is produced according to a conventional method. For example, a polyclonal antibody can be prepared by immunizing an animal (e.g., a rabbit) with the smaller molecule from a sulfated fucogalactan of the present invention or a salt thereof along with an adjuvant. Furthermore, a monoclonal antibody can be prepared by fusing melanoma cells with antibody-producing B cells obtained by immunization with an antigen, selecting a hybridoma producing the antibody of interest and culturing the cell. Such an antibody can be used for the purification of the smaller molecule from a sulfated fucogalactan of the present invention or a salt thereof. Furthermore, an antibody that recognizes the smaller molecule from a sulfated fucogalactan of the present invention or a salt thereof is useful for the analysis of the mode of action of inhibiting fertilization, the mode of action of inhibiting viral infection, in vivo metabolism or the like of a sulfated fucogalactan, a smaller molecule from a sulfated fucogalactan, or a salt thereof.

Additionally, a smaller molecule obtained by allowing the sulfated fucogalactan-degrading enzyme of the present invention to act on a sulfated fucogalactan or a salt thereof (i.e., an oligosaccharide) can be used as a reagent for glycotechnology. A substance that is very useful as a reagent for glycotechnology can be provided, for example, by subjecting the smaller molecule to amination with 2-aminopyridine (PA-labeling) according to the method as described in JP-B 5-65108 to prepare a PA-derivative of the smaller molecule.

According to the method for producing a smaller molecule from a sulfated fucogalactan of the present invention, the yield of the smaller molecule can be increased by deacetylating the sulfated fucogalactan. Deacetylation methods include, but are not limited to, a method of treatment in an alkaline aqueous solution and a method of treatment with a deacetylase. For example, the yield of the smaller molecule can be increased by deacetylating a sulfated fucogalactan in a 1 N sodium hydroxide solution at 25° C. for 24 hours. Thus, either a sulfated fucogalactan or a deacetylated sulfated fucogalactan may be preferably used as a raw material according to the method for producing a smaller molecule of the present invention.

EXAMPLES

The following examples further illustrate the present invention in detail but are not to be construed to limit the scope thereof.

Referential Example 1

Preparation of Sulfated Fucogalactan

2 Kg of dried *Kjellmaniella crassifolia* was disrupted using a cutter mill (Masuko Sangyo) equipped with a screen having a pore diameter of 1 mm, stirred in 20 L of 80% ethanol at 25° C. for 3 hours, filtered and washed. The resulting residue was suspended in 20 L of 30 mM imidazole buffer (pH 8.2) containing 50 mM calcium chloride, 100 mM sodium chloride, 10% ethanol and 1 U of an endo-type sulfated fucose-containing polysaccharide-degrading enzyme. The endo-type sulfated fucose-containing polysaccharide-degrading enzyme was obtained from a culture of *Alteromonas* sp. SN-1009 (deposited at International Patent Organism Depositary, National Institute of Advanced Industrial Science and Technology, AIST Tsukuba Central 6, 1-1, Higashi 1-chome, Tsukuba-shi, Ibaraki 305-8566, Japan on Feb. 13, 1996 under accession number FERM P-15436, and deposited at International Patent Organism Depositary, National Institute of Advanced Industrial Science and Technology under accession number FERM BP-5747 (date of request for transmission to international depositary authority: Nov. 15, 1996)) as described in WO 97/26896. The high viscosity and elasticity due to sulfated fucose-containing polysaccharides having high molecular weight were completely lost after the suspension was stirred at 25° C. for 2 days. The suspension was filtered through a stainless steel screen having a pore diameter of 32 µm to remove smaller molecules from the sulfated fucose-containing polysaccharides, and then washed. The resulting residue was suspended in 40 L of sodium phosphate buffer (pH 6.6) containing 100 mM sodium chloride, 10% ethanol and 4 g of alginate lyase K (Nagase Biochemicals). The suspension was stirred at 25° C. for 4 days, and then centrifuged to obtain a supernatant. The supernatant was concentrated to 2 L using an ultrafiltration device equipped with hollow fibers with exclusion molecular weight of 100,000 to remove smaller molecules from alginic acid contained in the supernatant. The solvent of the concentrate was exchanged for 100 mM sodium chloride containing 10% ethanol. An equal volume of 400 mM calcium acetate was added to the solution. After stirring, the mixture was centrifuged. 1 N hydrochloric acid was added to the resulting supernatant to adjust the pH to 2.0 while cooling on ice. The formed precipitate was removed by centrifugation. 1 N sodium hydroxide was added to the resulting supernatant to adjust the pH to 8.0. The solution was concentrated to 1 L by ultrafiltration and the solvent was exchanged for 100 mM sodium chloride. The formed precipitate was removed by centrifugation. The following procedure was carried out in order to remove hydrophobic substances in the resulting supernatant. Sodium chloride was added to the supernatant at a final concentration of 1 M. The mixture was loaded onto a 3-L Phenyl-Cellulofine column (Seikagaku Corporation) equilibrated with 1 M sodium chloride and flow-through fractions were collected. The fractions were concentrated using an ultrafiltration device, subjected to solvent exchange for 20 mM sodium chloride and lyophilized. The weight of the lyophilization product was 29.3 g.

15 g of the lyophilization product was dissolved in 1.5 L of 50 mM tris-hydrochloride buffer containing 400 mM sodium chloride and 9 U of an endo-type fucoidan-degrading enzyme. The endo-type fucoidan-degrading enzyme was obtained from a culture of *Flavobactrium* sp. SA-0082 (deposited at International Patent Organism Depositary, National Institute of Advanced Industrial Science and Technology, AIST Tsukuba Central 6, 1-1, Higashi 1-chome, Tsukuba-shi, Ibaraki 305-8566, Japan on Mar. 29, 1995 under accession number FERM P-14872, and deposited at International Patent Organism Depositary, National Institute of Advanced Industrial Science and Technology under accession number FERM BP-5402 (date of request for transmission to international depositary authority: Feb. 15, 1996)) as described in WO 97/26896. The solution was reacted at 25° C. for 6 days and then concentrated to about 300 ml using an evaporator. The concentrate was placed in a dialysis tube with exclusion molecular weight of 3500 and thoroughly dialyzed to remove smaller molecules from the sulfated fucoglucuronomannans. The solution retained in the dialysis tube was loaded onto a 4-L DEAE-Cellulofine A-800 (Chisso Corporation) equilibrated with 50 mM sodium chloride. After adequately washing with 50 mM sodium chloride, elution was carried out with a gradient of 50 to 650 mM sodium chloride. Full elution from the column was further carried out with 650 mM sodium chloride. The fraction eluted with 650 mM sodium chloride was collected as a sulfated fucogalactan fraction, concentrated using an ultrafiltration device with exclusion molecular weight of 100,000, subjected to solvent exchange for 10 mM sodium chloride and lyophilized to obtain 0.85 g of a lyophilization product of the sulfated fucogalactan fraction. The saccharide composition of the fraction was analyzed. The amount of fucose was determined as described in Journal of Biological Chemistry, 175:595 (1948).

The dried product of the sulfated fucogalactan was dissolved in 1 N hydrochloric acid at a final concentration of 0.5%. The solution was treated at 110° C. for 2 hours to hydrolyze into constituting monosaccharides. Reducing ends of the monosaccharides resulted from the hydrolysis were subjected to pyridyl-(2)-amination (PA-labeling) using GlycoTAG (Takara Shuzo) and GlycoTAG Reagent Kit (Takara Shuzo) to determine the ratio of constituting saccharides using HPLC. The HPLC was carried out as follows.

Instrument: L-6200 (Hitachi);
Column: Palpak Type A (4.6 mm×150 mm; Takara Shuzo);
Eluent: 700 mM borate buffer (pH 9.0):acetonitrile =9:1;
Detection: excitation wavelength at 310 nm and emission wavelength at 380 nm using fluorescence detector F-1150 (Hitachi);
Flow rate: 0.3 ml/minute; and
Column temperature: 65° C.

The amount of uronic acid was determined as described in Analytical Biochemistry, 4:330 (1962). Furthermore, the content of sulfate was determined as described in Biochemical Journal, 84:106 (1962).

As a result, the sulfated fucogalactan contained galactose and fucose as constituting saccharides at a molar ratio of about 2:1. Substantially no uronic acid or other neutral sugar was contained therein. The molar ratio of fucose and sulfate group was about 1:2.

Referential Example 2

Method for Measuring Activity of Sulfated Fucogalactan-Degrading Enzyme

An activity of degrading a sulfated fucogalactan was measured using the sulfated fucogalactan fraction obtained in Referential Example 1 as follows. Briefly, 60 µl of 50 mM imidazole-hydrochloride buffer (pH 7.5), 4.8 µl of 2.5% solution of the sulfated fucogalactan fraction, 6 µl of 4 M sodium chloride, 37.2 µl of water and 12 µl of a sulfated fucogalactan-degrading enzyme were mixed together. After reacting at 37° C. for 3 hours, the reaction mixture was treated at 100° C. for 10 minutes. After centrifugation, 100 µl of the supernatant was analyzed using HPLC to determine the degree of conversion into a smaller molecule. As controls, a reaction mixture obtained by a reaction under the similar conditions in which the buffer used for dissolving the sulfated fucogalactan-degrading enzyme was used in place of the enzyme and a reaction mixture obtained by a reaction in which water was used in place of the sulfated fucogalactan fraction were prepared, and similarly analyzed using HPLC.

One unit of an enzyme is defined as an amount of the enzyme that cleaves 1 µmol of galactosyl bonds in the sulfated fucogalactan fraction in 1 minute in the above-mentioned reaction system. The amount of cleaved galactosyl bond was calculated according to the following equation.

$$\{(4.8 \times 1000 \times 2.5/100)MG\} \times \{(MG/M)-1\} \times \{1/(180 \times 0.012)\} = U/ml$$

4.8×1000×2.5/100: sulfated fucogalactan added to the reaction system (μg);
MG: average molecular weight of sulfated fucogalactan in the fraction as a substrate;
M: average molecular weight of reaction product;
(MG/M)-1: number of bonds cleaved by the enzyme in one molecule of the sulfated fucogalactan;
180: reaction time (minutes); and
0.012: volume of enzyme solution (ml).

The HPLC was carried out as follows.
Instrument: L-6200 (Hitachi);
Column: OHpak SB-806HQ (8×300 mm; Showa Denko);
Eluent : 50 mM sodium chloride containing 5 mM sodium azide;
Detection: Differential Refractive Index Detector (Shodex RI-71, Showa Denko);
Flow rate: 1 ml/minute; and
Column temperature: 25° C.

The following procedure was carried out in order to determine the average molecular weight of the reaction product. Commercially available pullulan (STANDARD P-82, Showa Denko) of which the molecular weight was known was analyzed under the same conditions as those for the above-mentioned HPLC analysis. The relationship between the molecular weight of pullulan and retention time was expressed as a curve, which was used as a standard curve for determining the molecular weight of the enzymatic reaction product.

Referential Example 3

Preparation of Sulfated Fucogalactan-Degrading Enzyme

The sulfated fucogalactan-degrading enzyme as described in Referential Example 2 was prepared as follows. *Flavobacterium* sp. SA-0082 (FERM BP-5402) was inoculated into 600 ml of a medium consisting of artificial seawater (Jamarine Laboratory) containing 0.1% glucose, 1.0% peptone and 0.05% yeast extract (pH 7.5) which had been sterilized at 120° C. for 20 minutes, and cultured at 24° C. for 23 hours to prepare a seed culture. 20 L of a medium consisting of artificial seawater containing 0.2% sulfated fucose-containing polysaccharide fraction from *Kjellmaniella crassifolial,* 2.0% peptone, 0.01% yeast extract and 0.01% antifoaming agent (KM70, Shin-Etsu Chemical) (pH 7.5) was placed in 30 L jar fermentor and sterilized at 120° C. for 20 minutes. After cooling, 600 ml of the seed culture was inoculated into the medium and cultured at 24° C. for 23 hours with aeration of 10 l/minute and stirring at 125 rpm. After cultivation, the culture was centrifuged to collect cells.

The cells were suspended in 1,200 ml of 10 mM tris-hydrochloride buffer (pH 8.0) containing 0.4 M sodium chloride, sonicated and centrifuged to obtain a cell extract. The cell extract was adequately dialyzed against the same buffer and centrifuged to obtain a supernatant. Ammonium sulfate was added to the supernatant at a final concentration of 90% saturation. The formed precipitate collected by centrifugation was dissolved in 150 ml of 10 mM tris-hydrochloride buffer (pH 8.0) containing 50 mM sodium chloride and adequately dialyzed against the same buffer. A supernatant obtained by centrifugation was loaded onto a 500-mL DEAE-Sepharose FF column (Amersham Pharmacia) equilibrated with the same buffer. After washing with the same buffer, elution was then carried out with a gradient of 50 mM to 600 mM sodium chloride to collect an active fraction.

The active fraction was adequately dialyzed against 10 mM tris-hydrochloride buffer (pH 8.0) containing 0.1 M sodium chloride, loaded onto a 100-mL DEAE-Cellulofine A-800 column (Chisso Corporation) equilibrated with the same buffer. After washing with the same buffer, elution was carried out with a gradient of 0.1 M to 0.4 M sodium chloride to collect an active fraction. Sodium chloride was added to the active fraction at a final concentration of 4 M. The fraction was loaded onto a 20-mL Phenyl-Cellulofine column (Chisso Corporation) equilibrated with 10 mM tris-hydrochloride buffer (pH 8.0) containing 4 M sodium chloride. After washing with the same buffer, elution was carried out with a gradient of 4 M to 1 M sodium chloride. Full elution was further carried out with 10 mM tris-hydrochloride buffer (pH 8.0) containing 1 M sodium chloride to collect an active fraction. Sodium chloride was added to the active fraction at a final concentration of 3 M. The fraction was loaded onto a 10-mL Phenyl-Cellulofine column (Chisso Corporation) equilibrated with 10 mM tris-hydrochloride buffer (pH 8.0) containing 3 M sodium chloride. After washing with the same buffer, elution was carried out with a gradient of 3 M to 0.5 M sodium chloride. Full elution was further carried out with 10 mM tris-hydrochloride buffer (pH 8.0) containing 0.5 M sodium chloride to collect an active fraction as a purified enzyme.

Example 1

Cloning of Sulfated Fucogalactan-Degrading Enzyme Gene (1) Preparation of Genomic DNA

*Flavobactrium* sp. SA-0082 (FERM BP-5402) is a strain producing a sulfated fucogalactan-degrading enzyme. *Flavobactrium* sp. SA-0082 was inoculated into a 2-L Erlenmeyer flask containing 500 ml of a medium consisting of artificial seawater (Jamarine Laboratory) containing 0.25% glucose, 1.0% peptone and 0.05% yeast extract (pH 8.0) which had been sterilized at 120° C. for 20 minutes and cultured at 25° C. for 23 hours. After cultivation, a half of cells collected by centrifuging the culture were suspended in 10 ml of an extraction buffer (50 mM tris-hydrochloride buffer (pH 8.0), 100 mM ethylenediaminetetraacetic acid (EDTA)). 1 ml of a solution of lysozyme (Sigma) at a concentration of 20 mg/ml in the extraction buffer was added thereto. The mixture was incubated in an ice bath for 30 minutes. 10 ml of a proteinase K solution (1 mg/ml proteinase K (Takara Shuzo), 50 mM tris-hydrochloride buffer (pH 8.0), 100 mM EDTA, 1% SDS) was added thereto. The mixture was incubated at 50° C. for 2 hours. The mixture was cooled to room temperature, and an equal volume of phenol saturated with TE buffer (10 mM tris-hydrochloride buffer (pH 8.0), 1 mM EDTA) was added thereto. The mixture was stirred gently for 1 hour. After centrifugation at 10000 rpm for 20 minutes, the upper layer was collected. An equal volume of a 1:1 mixture of phenol saturated with TE buffer/chloroform was added to the upper layer. The mixture was stirred gently. After centrifugation at 10000 rpm for 20 minutes, the upper layer was recovered. The phenol/chloroform extraction was carried out again. Sodium chloride was added to the aqueous phase at a final concentration of 0.1 M. Two volumes of ethanol was further added to the mixture to deposit DNA. The DNA was wound using a glass bar, rinsed with 80% ethanol and then slightly air dried. The genomic DNA was dissolved in 20 ml of a solution containing ribonuclease A (Sigma) at a concentration of 20 µg/ml in TE buffer. The mixture was incubated at 37° C. for 5 hours to degraded RNA. DNA was collect by phenol extraction and phenol/chloroform extraction followed by addition of ethanol as described above, and suspended in 5 ml of TE buffer. About 20 mg of genomic DNA was obtained by the procedure.

(2) Construction of Genomic DNA Library

100 µg of the genomic DNA prepared in Example 1-(1) was partially digested by treatment with 10 U of a restriction enzyme Sau3AI (Takara Shuzo) at 37° C. for 1 minute and 40 seconds. The mixture was subjected to phenol/chloroform extraction and the upper layer was collected. A 1/10 volume of a 3 M sodium acetate aqueous solution (pH 5.0) and 2.5 volumes of ethanol were added to the upper layer to precipitate DNA. The precipitate was collected by centrifugation, rinsed with 80% ethanol and air dried. The thus obtained partial digestion product was subjected to size fractionation by 1.25-5 M sodium chloride density gradient ultracentrifugation, and DNA was collected from fractions containing DNAs having sizes ranging from 10 to 20 kbp by ethanol precipitation. 0.2 µg of the partial digestion product of the genomic DNA and 0.6 µg of λBlueSTAR BamHI Arm (Novagen) were mixed together and ligated to each other using DNA Ligation Kit (Takara Shuzo). The ligation mixture was packaged into lambda phage using Gigapack II Gold Kit (Stratagene) to construct a *Flavobactrium* sp. SA-0082 genomic DNA library.

(3) Determination of Amino Acid Sequence of Sulfated Fucogalactan-Degrading Enzyme 84 µg of the purified sulfated fucogalactan-degrading enzyme protein obtained from *Flavobactrium* sp. SA-0082 as described in Referential Example 3 was applied to a column for desalting (Fast Desalting Column PC 3.2/10, Pharmacia) equilibrated with water and eluted with water to exchange the buffer. The eluate was collected in a glass vial and concentrated to dryness. The glass vial containing the sample was placed in a larger glass test tube containing 200 µl of pyridine, 40 µl of 4-vinylpyridine, 40 µl of tri-N-butylphosphine and 200 µl of water. The glass test tube was sealed, and a reaction was carried out at 100° C. for 7 minutes for pyridyl-ethylation. After reaction, the glass vial was taken out and subjected to several rounds of azeotropic distillation with water to remove volatile components.

The thus obtained pyridyl-ethylated sulfated fucogalactan-degrading enzyme protein was digested at 37° C. overnight after adding 30 µl of 100 mM tris-hydrochloride buffer (pH 9.2) containing 8 M urea, 30 µl of 100 mM tris-hydrochloride buffer (pH 9.2) and 40 pmol of Achromobacter protease I (Takara Shuzo) thereto. Peptide fragments were purified from the resulting digestion product using an HPLC system (SMART System, Pharmacia). µRPC C2/C18 SC 2.1/10 (Pharmacia) was used for the column, and the flow rate was 100 µg/ml. Elution was carried out using a linear gradient method as follows. A 0.1% trifluoroacetic acid aqueous solution (Eluent A) and acetonitrile containing 0.1% trifluoroacetic acid (Eluent B) were used for elution. The percentage of the Eluent B was 0% at the time of application of the sample, and the percentage of the Eluent B was elevated up to 40% in 100 minutes. Among the eluted fractions, fractions containing peptides were subjected to amino acid sequence analyses. Then, partial amino acid sequences S21 (SEQ ID NO:1), S23 (SEQ ID NO:2), S39 (SEQ ID NO:3), S42 (SEQ ID NO:4), S49 (SEQ ID NO:5), S162 (SEQ ID NO:6), and S292 (SEQ ID NO:7) were determined.

(4) Determination of Nucleotide Sequence of Sulfated Fucogalactan-Degrading Enzyme Gene 1.2 µg of the genomic DNA prepared in Example 1-(1) was digested at 37° C. for 5 hours with 30 U of a restriction enzyme BglII, EcoRI, EcoT14I, EcoT22I, HindIII, NcoI, PstI, SpeI or XbaI (all from Takara Shuzo). The digestion products were subjected to phenol/chloroform extraction, and collected by ethanol precipitation. 50 ng of a cassette was mixed with about 0.6 µg of each digestion product and ligated using DNA Ligation Kit (Takara Shuzo). The following cassettes were used for the respective digestion products: Sau3AI cassette for the BglII digestion product; EcoRI cassette for the EcoRI digestion product; PstI cassette for the EcoT22I digestion product and the PstI digestion product; HindIII cassette for the HindIII digestion product; and XbaI cassette for the SpeI digestion product and the XbaI digestion product (all cassette DNAs from Takara Shuzo). NcoI cassette prepared using two synthetic oligonucleotides (SEQ ID NOS:8 and 9) was ligated with the EcoT14I digestion product and the NcoI digestion product. Each reaction mixture was collected by ethanol precipitation and dissolved in 5 µl of water and used as a template DNA in the PCR method using the cassette DNA.

Mixed oligonucleotides in the same directions as those of the amino acid sequences, SFG-391F primer (SEQ ID NO:10) and SFG-392F primer (SEQ ID NO:11), were synthesized on the basis of the sequence of amino acids 1 to 7 and the sequence of amino acids 8 to 15 of the partial amino acid sequence S39 (SEQ ID NO:3) determined in Example 1-(3). In addition, mixed oligonucleotides in the same directions as those of the amino acid sequences, SFG-421F primer (SEQ ID NO:12) on the basis of the sequence of amino acids 1 to 8 of S42 (SEQ ID NO:4), as well as SFG-422F primer (SEQ ID NO:13) and SFG-423F primer (SEQ ID NO:14) on the basis of the sequence of amino acids 6 to 14 were synthesized.

8 µl of 2.5 mM dNTP mix, 20 pmol of a cassette primer C1 (Takara Shuzo), 100 pmol of the mixed oligonucleotide SFG-391F (SEQ ID NO:10) or SFG-421F (SEQ ID NO:12) and sterile water to a total volume of 50 µl were mixed together, and Ampliwax PCR Gem100 (Takara Shuzo) was added thereto. The mixture was heated at 70° C. for 3 minutes and then allowed to stand at room temperature for 10 minutes. 10 µl of 10×Ex Taq amplification buffer (Takara Shuzo), 1 µl of the previously prepared template DNA, 2 units of TaKaRa Ex Taq DNA polymerase (Takara Shuzo) and sterile water to a total volume of 100 µl were added thereto. The mixture was subjected to an amplification reaction using an automated gene amplification apparatus (a thermal cycler) TaKaRa PCR Thermal Cycler (Takara Shuzo). The PCR was carried out as follows: 30 cycles of denaturation at 94° C. for 0.5 minute, annealing at 45° C. for 1 minute, and synthesis reaction at 72° C. for 3 minutes.

Next, a second PCR was carried out using a portion of the first PCR reaction mixture as a template DNA. Specifically, 8 µl of 2.5 mM dNTP mix, 20 pmol of a cassette primer C2 (Takara Shuzo), 100 pmol of the mixed oligonucleotide SFG-392F (SEQ ID NO:11), SFG-422F (SEQ ID NO:13) or SFG-423F (SEQ ID NO:14) and sterile water to a total volume of 50 µl were mixed together, and Ampliwax PCR Gem100 was added thereto. The mixture was heated at 70° C. for 3 minutes and then allowed to stand at room temperature for 10 minutes. 10 µl of 10×Ex Taq amplification buffer (Takara Shuzo), 1 µl of the first PCR reaction mixture, 2 U of TaKaRa Ex Taq DNA polymerase and sterile water to a total volume of 100 µl were added thereto. The mixture was subjected to an amplification reaction as follows: 25 cycles of denaturation at 94° C. for 0.5 minute, annealing at 45° C. for 1 minute, and synthesis reaction at 72° C. for 3 minutes. In parallel, reaction mixtures containing only the cassette primer C2 or the mixed oligonucleotide as controls for nonspecific amplification products from the respective primers were subjected to PCRs.

The reaction mixtures were analyzed by agarose gel electrophoresis, and specifically amplified bands were detected for many reaction mixtures as compared with the controls for nonspecific amplification products. Among these, intense amplified bands were extracted and purified from reaction mixtures with relatively low background, i.e., an about 0.8-kb band from the reaction mixture of the SpeI digestion product/XbaI cassette/C2-SFG-392F primer; an about 1.4-kb band from the reaction mixture of the HindIII digestion product/HindIII cassette/C2-SFG-423F primer; and an about 1.1-kb band from the reaction mixture of the EcoRI digestion product/EcoRI cassette/C2-SFG-423F primer. The DNA fragment was mixed with pT7blue T-vector (Novagen), and ligated using DNA Ligation Kit. The ligation mixture was used to transform Escherichia coli JM109. White colonies grown on plates of L medium containing 100 µg/ml ampicillin, 0.004% X-Gal and 1 mM IPTG were selected. Each transformant was inoculated into liquid L medium containing 100 µg/ml ampicillin. After culturing at 37° C. overnight, plasmid DNAs were prepared from the cultured cells according to the alkali lysis method. Plasmids having inserted bands of sizes of interest were selected and designated as S3921, H4231 and R4231. The nucleotide sequences of the inserts were analyzed according to the dideoxy method. In each of S3921 and R4231, a region encoding the partial amino acid sequence following the sequence of the primer used for the second PCR was found. The nucleotide sequences of the inserted fragments in S3921 and R4231 were partially overlapped with each other. The length of the combined nucleotide sequence was about 1.6 kbp. A portion of a reading frame containing regions encoding the partial amino acid sequences S42 (SEQ ID NO:4), S162 (SEQ ID NO:6), S23 (SEQ ID NO:2), S49 (SEQ ID NO:5), S292 (SEQ ID NO:7) and S39 (SEQ ID NO:3) was contained in the combined sequence. Thus, it was shown that this fragment contains a portion of a sulfated fucogalactan-degrading enzyme gene.

Furthermore, mixed oligonucleotides in the opposite directions to those of the amino acid sequences, SFG-231R primer (SEQ ID NO:15) and SPG-232R primer (SEQ ID NO:16) on the basis of the sequence of amino acids 6 to 13 of the partial amino acid sequence S23 (SEQ ID NO:2) determined in Example 1-(3) as well as SFG-239R primer (SEQ ID NO:17) and SFG-230R primer (SEQ ID NO:18) on the basis of the sequence of amino acids 3 to 9, were synthesized. Screening from a cassette library was examined in a manner similar to the above. The reaction mixtures were analyzed by agarose gel electrophoresis, and specifically amplified bands were detected for many reaction mixtures as compared with controls for nonspecific amplification products. Among these, an intense amplified band was extracted and purified from reaction mixture with relatively low background, i.e., an about 1.4-kb band from the reaction mixture of the EcoT14I digestion product/NcoI cassette/C2-SFG-239R primer. The DNA fragment was ligated with pT7blue T-vector, and a plasmid having an inserted band of the size of interest was selected in a manner similar to that as described above and designated as T2392. The nucleotide sequence of the insert was analyzed. The nucleotide sequence was partially overlapped with the 1.6-kbp nucleotide sequence analyzed above. The length of the determined combined nucleotide sequence was about 2.8 kbp. A reading frame of 1602 nucleotides (including the stop codon) was found therein. Regions highly homologous to the partial amino acid sequences determined in Example 1-(3) were found in the amino acid sequence encoded by the reading frame. The 1602-bp reading frame was designated as sfgA.

Sequences corresponding to the partial amino acid sequences of the sulfated fucogalactan-degrading enzyme determined in Example 1-(3), S21 (SEQ ID NO:1), S23 (SEQ ID NO:2), S39 (SEQ ID NO:3), S42 (SEQ ID NO:4) and S292 (SEQ ID NO:7), as well as sequences highly homologous to the partial amino acid sequences S49 (SEQ ID NO:5) and S162 (SQ ID NO:6) were found in the amino acid sequence encoded by sfgA. As described above, the amino acid sequence encoded by sfgA contained sequences corresponding to or highly homologous to all of the amino acid sequences determined by analyses of the partial amino acid sequence of the sulfated fucogalactan-degrading enzyme in Example 1-(3). Therefore, it was considered that sfgA substantially encoded the sulfated fucogalactan-degrading enzyme from Flavobactrium sp. SA-0082.

On the other hand, a region encoding a sequence starting from the 15th amino acid in the partial amino acid sequence S42 (SEQ ID NO:4) was found following the sequence of SFG-423F used for the second PCR in H4231, although the sequence for the 19th and 20th amino acids were different. The entire nucleotide sequence of the insert in H4231 was determined. The sequence was partially overlapped with the above-mentioned 2.8-kbp nucleotide sequence. Thus, it was found that a portion of a reading frame highly homologous to sfgA existed upstream from sfgA.

(5) Isolation of SfgA Homolog

A clone containing a sulfated fucogalactan-degrading enzyme gene was screened by the plaque hybridization method from the Flavobactrium sp. SA-0082 genomic DNA library prepared in Example 1-(2) as follows. Escherichia coli ER 1647 cells were infected with the genomic DNA phage library, and about 1300 plaques were formed on each of three L medium plates in 10 cm×14 cm petri dishes. The phages were transferred to nylon membranes Hybond-N+ (Amersham Pharmacia Biotech) by contacting the membranes with the plates for about 2 minutes. The nylon membranes were subjected to denaturation in a solution containing 0.5 M sodium hydroxide and 1.5 M sodium chloride for 5 minutes, followed by neutralization in a solution containing 0.5 M tris-hydrochloride buffer (pH 7.0) and 3 M sodium chloride for 5 minutes, then rinsed in 2×SSC and air dried. The nylon membranes were heated at 80° C. for 1 hour to immobilize the DNA.

About 15 µg of the T2392 plasmid DNA obtained in Example 1-(4) was digested with EcoRI and NdeI at sites in the vector, and the released about 1.4-kb fragment containing to a part of the sulfated fucogalactan-degrading enzyme gene was extracted and purified. The DNA fragment was labeled with digoxigenin using DIG DNA Labeling and Detection Kit (Roche Diagnostic), and subjected to plaque hybridization according to the instruction manual as follows. The filters prepared as described above were subjected to prehybridization at 60° C. for 4 hours in a hybridization solution. The labeled probe was added thereto after heat denaturation at a final concentration of about 60 ng/ml. Hybridization was carried out at 60° C. overnight. After hybridization, washing was carried out twice in 2×SSC and 0.1% SDS at room temperature for 5 minutes followed by twice in 0.5×SSC and 0.1% SDS at 45° C. for 15 minutes. Then, detection was carried out using the detection kit. As a result, 24 positive signals were observed. Plaques around the positions corresponding to the positive signals were taken from the original plates and suspended in SM buffer (50 mM tris-HCl (pH 7.5), 0.1 M NaCl, 7 mM MgSO$_4$, 0.01% gelatin) to collect phages.

Some of the thus obtained phage suspensions were used to form plaques on new plates. The same procedure was repeated. As a result, five phages that resulted in positive signals were isolated.

According to the instruction manual of λBlueSTAR (Novagen), *Escherichia coli* BM25.8 cells were infected with the thus obtained phages and then spread on L medium plates containing 100 μg/ml of amplicillin, and ampicillin-resistant colonies were selected to convert the phages into plasmids. A colony for each clone was inoculated into liquid L medium containing 100 μg/ml of ampicillin. After culturing at 37° C. overnight, plasmid DNAs were prepared from the cultures according to the alkali lysis method. The plasmid DNA was used to transform *Escherichia coli* JM109 (Takara Shuzo). A colony for each clone was inoculated into liquid L medium containing 100 μg/ml ampicillin. After culturing at 37° C. overnight, plasmid DNAs were prepared from the cultures according to the alkali lysis method again. The thus obtained plasmids for the respective clones were designated as pBsfg5, pBsfg7, pBsfg13, pBsfg17 and pBsfg18. The plasmids were digested with appropriate restriction enzymes and subjected to agarose gel electrophoresis. Restriction maps were prepare for the respective inserts to analyze them. As a result, plural bands having similar sizes were detected after staining the agarose gel with ethidium chloride. Thus, it was assumed that about 3- to 14-kbp fragments corresponding to almost the same positions in the genomic DNA were inserted into the plasmids.

Among the plasmids obtained as described above, pBsfg17 which had an about 7-kbp insert was subjected to further analysis of the insert. Specifically, about 1 μg of pBsfg17 was digested with KpnI, and the released fragment of about 7 kbp was extracted and purified. The KpnI fragment was mixed and ligated using DNA Ligation Kit with an ampicillin-resistant vector pUC119 (Takara Shuzo) digested with KpnI. The ligation mixture was used to transform *Escherichia coli* JM109. White colonies grown on L medium plates containing 100 μg/ml ampicillin, 0.004% X-Gal and 1 mM IPTG were selected. Each transformant was inoculated into liquid L medium containing 100 μg/ml ampicillin. After culturing at 37° C. overnight, plasmid DNAs were prepared from the cultured cells according to the alkali lysis method. The plasmid DNAs were digested with restriction enzymes and analyzed by agarose gel electrophoresis. As a result, pUC17K1 and pUC17K3 in which an about 7-kbp DNA derived from pBsfg17 was inserted into the vector DNA in different directions were obtained. The nucleotide sequences were analyzed for the plasmids in detail according to the dideoxy method directly by the primer extension method or after restriction enzyme digestion followed by subcloning or the like. As a result, sfgA A and a reading frame of 1626 nucleotides (including the stop codon) upstream from sfgA were found. The amino acid sequence encoded by the reading frame was highly homologous to the amino acid sequence encoded by sfgA. The reading frame was designated as sfgB.

Sequences highly homologous to the partial amino acid sequences of the sulfated fucogalactan-degrading enzyme, S21 (SEQ ID NO:1), S23 (SEQ ID NO:2), S39 (SEQ ID NO:3), S42 (SEQ ID NO:4), S49 (SEQ ID NO:5), S162 (SEQ ID NO:6) and S292 (SEQ ID NO:7), were found also in the amino acid sequence encoded by sfgB. sfgA and sfgB were compared to each other and it was found that the nucleotide and amino acid sequence homologies were high (about 67% and about 59%, respectively). Thus, it was considered that sfgb also encodes a polypeptide having an activity of degrading a sulfated fucogalactan. As described above, the entire nucleotide sequences of a gene presumed to encode a polypeptide having an activity of degrading a sulfated fucogalactan (sfgA) and a gene highly homologous to this gene (sfgB) were determined. The nucleotide sequence of sfgA and the amino acid sequence encoded by sfgA are shown in SEQ ID NOS:19 and 20, respectively. Furthermore, the nucleotide sequence of sfgB and the amino acid sequence encoded by sfgB are shown in SEQ ID NOS:21 and 22, respectively.

Thus, a gene presumed to substantially encode a sulfated fucogalactan-degrading enzyme (sfgA) and a gene that is homologous to this gene and is presumed to encode a novel polypeptide having an activity of degrading a sulfated fucogalactan (sfgB) were determined according to the present invention.

(6) Sulfated Fucogalactan-Degrading Enzyme Derived from SfgA Gene

The full length sfgA gene was inserted into an expression vector to express a sulfated fucogalactan-degrading enzyme. However, since the activity was low, expression of a polypeptide from which the N-terminus had been deleted was examined as follows.

An expression vector for the gene presumed to substantially encode a sulfated fucogalactan-degrading enzyme (sfgA) obtained in Example 1-(5) was constructed as follows. A primer sfgAL5 (SEQ ID NO:23) was designed such that the N-terminal amino acid to the 23rd amino acid in the encoded protein is deleted and an NdeI site is introduced. A primer sfgAR4 (SEQ ID NO:24) was designed such that it has an XhoI recognition site in place of the stop codon and hybridizes to a strand opposite to the strand to which the primer sfgAL5 hybridizes. A PCR was carried out as follows using these two primers as well as the *Flavobactrium* sp. SA-0082 chromosomal DNA as a template. 10 pmol each of the primers sfgAL5 and sfgAR4, 10 ng of the chromosomal DNA as a template, 5 μl of 10×Ex Taq amplification buffer, 8 μl of dNTP mix, 0.5 μl of TaKaRa Ex Taq and sterile water to a total volume of 50 μl were added to a 0.5-ml PCR tube. The tube was placed in an automated gene amplification apparatus (a thermal cycler, Takara Shuzo). After denaturation at 94° C. for 2 minutes, 25 cycles of denaturation at 94° C. for 1 minute, annealing at 55° C. for 2 minutes, and synthesis reaction at 72° C. for 2 minutes were carried out. The amplified DNA fragment was cleaved with NdeI and XhoI, and separated by electrophoresis on 1.0% agarose gel. An about 1.5-kb NdeI-XhoI fragment encoding an amino acid sequence starting from the 24th amino acid was excised, extracted and purified.

The about 1.5-kb NdeI-XhoI fragment prepared as described above was inserted into an expression vector that utilizes the T7 lac promoter, pET16b (Novagen), which had been cleaved at the NdeI site and the XhoI site. The construct was designated as pEA101. A protein in which 22 amino acids derived from the vector are added to both ends of a polypeptide consisting of the amino acid sequence encoded by sfgA starting from the 24th amino acid is expressed from this hybrid vector. Furthermore, it has a sequence consisting of 10 successive histidine residues (His.Tag) at the N-terminus. pEA101 was used to transform *Escherichia coli* BL21 (DE3) (Novagen). *Escherichia coli* BL21(DE3)/pEA101 was inoculated into 30 ml of liquid L medium containing 50 μg/ml ampicillin, and cultured at 37° C. overnight. The whole culture was inoculated into 3 l of fresh L medium containing 50 μg/ml ampicillin, and cultured at 37° C. at 200 rpm with aeration of 1.0 l/min until logarithmic growth phase. A 5-l minijar (Able) was used for cultivation. IPTG was added at a final concentration of 0.5 mM when turbidity (O.D. 600) reached 0.4. Cultivation was continued at 25° C. at 120 rpm with aeration of 1.0 l/min overnight. After cultivation, about 21 g of the cells were collected from the culture by centrifugation. About 7.0 g of the cells were subjected to purification as follows. The His.Tag in the N-terminal region was utilized for the purification using His.Tag Resin (Novagen). The cells were suspended in 40 ml of a Binding buffer (20 mM tris-HCl (pH 7.9), 500 mM NaCl, 5 mM imidazole), and disrupted by sonication. A supernatant obtained by centrifuging the sonicated suspension was applied to 10-ml His.Bind Resin to which Ni had been added and which had been equilibrated with the Binding buffer. The column was washed with 50 ml of the Binding buffer followed by 30 ml of a Wash buffer (40 mM tris-HCl (pH 7.9), 500 mM NaCl, 60 mM imidazole). The protein of interest was collected using 50 ml of an Elute buffer (20 mM tris-HCl (pH 7.9), 500 mM NaCl, 1 M imidazole). The protein of interest in a purified form was detected upon SDS-PAGE. The activity of degrading a sulfated fucogalactan was 580 mU/ml as measured according to the method as described in Referential Example 2. Thus, it was shown that the polypeptide encoded by sfgA had an activity of degrading a sulfated fucogalactan, and that the polypeptide encoded by sfgA corresponding to about 58 mU of the activity of degrading a sulfated fucogalactan was produced in 1 ml of the culture of *Escherichia coli* BL21(DE3)/pEA101 which has the gene of the present invention. The nucleotide sequence for the polypeptide encoded by sfgA lacking the N-terminus is shown in SEQ ID NO:27, and the amino acid sequence of the polypeptide is shown in SEQ ID NO:28. *Escherichia coli* harboring the plasmid pEA101 is indicated as *Escherichia coli* BL21(DE3)/pEA101 and deposited on Jun. 20, 2001 at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM P-18380, and deposited at International Patent Organism Depositary, National Institute of Advanced Industrial Science and Technology under accession number FERM BP-8149 (date of request for transmission to international depositary authority: Aug. 13, 2002).

(7) Sulfated Fucogalactan-Degrading Enzyme Derived from SfgB Gene

The full length sfgb gene was inserted into an expression vector to express a sulfated fucogalactan-degrading enzyme. However, since the activity was not detected, expression of a polypeptide from which the N-terminus had been deleted was examined as follows.

An expression vector for the gene encoding a novel polypeptide presumed to have an activity of degrading a sulfated fucogalactan (sfgB) obtained in Example 1-(5) was constructed. A primer sfgBL7 (SEQ ID NO:25) was designed such that the N-terminal amino acid to the 30th amino acid in the encoded protein is deleted and an NdeI site is introduced. A primer sfgBR3 (SEQ ID NO:26) was designed such that it has an XhoI recognition site in place of the stop codon and hybridizes to a strand opposite to the strand to which the primer sfgBL7 hybridizes. A PCR was carried out using these two primers as well as the *Flavobacterium* sp. SA-0082 chromosomal DNA as a template under conditions similar to those described in Example 1-(6). The amplified DNA fragment was cleaved with NdeI and XhoI, and separated by electrophoresis on 1.0% agarose gel. An about 1.5-kb NdeI-XhoI fragment encoding an amino acid sequence starting from the 31st amino acid was excised, extracted and purified. The fragment was inserted into pET16b which had been cleaved with the same enzymes. The construct was designated as pEB101. A protein in which 22 amino acids derived from the vector are added to both ends of a polypeptide consisting of the amino acid sequence encoded by sfgB starting from the 31st amino acid is expressed from this hybrid vector. Furthermore, it has a sequence consisting of 10 successive histidine residues (His.Tag) at the N-terminus.

pEB101 was used to transform *Escherichia coli* BL21 (DE3) (Novagen). *Escherichia coli* BL21(DE3)/pEB101 was inoculated into 30 ml of liquid L medium containing 50 μg/ml ampicillin, and cultured at 37° C. overnight. The whole culture was inoculated into 3 l of fresh L medium containing 50 μg/ml ampicillin, and cultured at 37° C. at 200 rpm with aeration of 1.0 l/min until logarithmic growth phase. A 5-l minijar (Able) was used for cultivation. IPTG was added at a final concentration of 0.5 mM when turbidity (O.D. 600) reached 0.4. Cultivation was further continued at 25° C. at 120 rpm with aeration of 1.0 l/min overnight. After cultivation, about 23 g of the cells were collected from the culture by centrifugation. About 7.7 g of the cells were subjected to purification as follows. The His.Tag in the N-terminal region was utilized for the purification using His.Tag Resin (Novagen). The cells were suspended in 50 ml of a Binding buffer (20 mM tris-HCl (pH 7.9), 500 mM NaCl, 5 mM imidazole), and disrupted by sonication. A supernatant obtained by centrifuging the sonicated suspension was applied to 20-ml His.Bind Resin to which Ni had been added and which had been equilibrated with the Binding buffer. The column was washed with 100 ml of the Binding buffer followed by 60 ml of a Wash buffer (40 mM tris-HCl (pH 7.9), 500 mM NaCl, 60 mM imidazole). The protein of interest was collected using 50 ml of an Elute buffer (20 mM tris-HCl (pH 7.9), 500 mM NaCl, 1 M imidazole). The protein of interest in a purified form was detected upon SDS-PAGE. The activity of degrading a sulfated fucogalactan was 3.05 mU/ml as measured according to the method as described in Referential Example 2. Thus, it was shown that the polypeptide encoded by sfgB had an activity of degrading a sulfated fucogalactan, and that the polypeptide encoded by sfgB corresponding to about 0.3 mU of the activity of degrading a sulfated fucogalactan was produced in 1 ml of the culture of *Escherichia coli* BL21(DE3)/pEB101 which has the gene of the present invention. The nucleotide sequence for the polypeptide encoded by sfgB lacking the N-terminus is shown in SEQ ID NO:29, and the amino acid sequence of the polypeptide is shown in SEQ ID NO:30. *Escherichia coli* harboring the plasmid pEB101 is indicated as *Escherichia coli* BL21(DE3)/pEB101 and is deposited on Jun. 20, 2001 at International Patent Organism Depositary, National Institute of Advanced Industrial Science and Technology, AIST Tsukuba Central 6, 1-1, Higashi 1-chome, Tsukuba-shi, Ibaraki 305-8566, Japan under accession number FERM P-18381, and deposited at International Patent Organism Depositary, National Institute of Advanced Industrial Science and Technology under accession number FERM BP-8150 (date of request for transmission to international depositary authority: Aug. 13, 2002).

Example 2

Homology Search of Sulfated Fucogalactan-Degrading Enzyme Gene

The amino acid sequences and the nucleotide sequences for the polypeptides each having an activity of a sulfated fucogalactan-degrading enzyme obtained in Example 1 were used to conduct homology searches. Calculation was carried out using a computer algorithm BLAST (version 2.0; Altschul et al., Nucleic Acids Res., 25:3389-3402, 1997) as a search program.

sfgA and sfgb were subjected to searches of a gene databases using the computer algorithm BLAST. As a result, the highest homology observed for the full length amino acid sequence encoded by sfgA was 8%, and the highest homology observed for the full length nucleotide sequence was 1%. For sfgB, the highest homologies observed for the encoded amino acid and nucleotide sequences were 7% and 1%, respectively.

Furthermore, homologies with the genes fdlA and fdlB which encode polypeptides having endo-type sulfated fucose-containing polysaccharide-degrading activities derived from *Flavobacterium* as described in WO 99/11797 were calculated using Maximum Matching in a search program DNASIS-Mac (Takara Shuzo). The nucleotide sequence homologies of sfgA to fdlA and fdlB were 54% and 52%, respectively. The encoded amino acid sequence homologies were 34% and 30%, respectively. The nucleotide sequence homologies of sfgB to fdlA and fdlB were 53% and 52%, respectively. The encoded amino acid sequence homologies were 33% and 30%, respectively.

The nucleotide and encoded amino acid sequence homologies between sfgA and sfgB were 69% and 59.4%, respectively.

Example 3

Effect of Deacetylation of Sulfated Fucogalactan 200 mg of the sulfated fucogalactan fraction as described in Referential Example 1 was dissolved in 20 ml of 1 N sodium hydroxide. The solution was allowed to stand at 25° C. for 24 hours. It is possible to selectively hydrolyze O-acetyl groups by this procedure. The thus obtained deacetylated sulfated fucogalactan was adequately dialyzed against 10% ethanol. The macromolecule fraction was lyophilized to obtain 137 mg of deacetylated sulfated fucogalactan.

The sulfated fucogalactan-degrading enzyme derived from the sfgA gene obtained in Example 1-(6) was allowed to act on the sulfated fucogalactan or the deacetylated sulfated fucogalactan, and the degrees of conversion into smaller molecules were determined using HPLC.

Specifically, 120 µl of 50 mM phosphate buffer (pH 8.0), 24 µl of 2.5% solution of the sulfated fucogalactan or the deacetylated sulfated fucogalactan, 12 µl of 4 M sodium chloride and 82.9 µl of water were mixed together. 1.1 µl of the sulfated fucogalactan-degrading enzyme (885 mU/ml) was mixed with each mixture. The resulting mixtures were reacted at 30° C. for 24 hours. The reaction mixtures were analyzed using HPLC according to the method as described in Referential Example 2 to compare the degrees of conversion of the substrates into smaller molecules. As a result, the average molecular weight observed after degradation of the sulfated fucogalactan as a substrate was about 160,000, whereas the molecular weight observed after degradation of the deacetylated sulfated fucogalactan as a substrate was about 10,000 or below. Thus, it was shown that if a sulfated fucogalactan oligosaccharide is to be obtained using the enzyme, an oligosaccharide with a lower molecular weight can be obtained by deacetylating the sulfated fucogalactan.

INDUSTRIAL APPLICABILITY

The present invention provides a gene encoding a polypeptide that has an activity of degrading a sulfated fucogalactan which is useful as a reagent for glycotechnology, for a structural analysis of a sulfated fucose-containing polysaccharide or for preparation of a smaller molecule from the polysaccharide, a method for producing the polypeptide using genetic engineering techniques, and a polypeptide obtainable by the method.

Sequence Listing Free Text

SEQ ID No:8: Description of Artificial Sequence: NcoI cassete1

SEQ ID No:9: Description of Artificial Sequence: NcoI cassete2

SEQ ID No:10: Description of Artificial Sequence: SFG-391F

SEQ ID No:11: Description of Artificial Sequence: SFG-392F

SEQ ID No:12: Description of Artificial Sequence: SFG-421F

SEQ ID No:13: Description of Artificial Sequence: SFG-422F

SEQ ID No:14: Description of Artificial Sequence: SFG-423F

SEQ ID No:15: Description of Artificial Sequence: SFG-231R

SEQ ID No:16: Description of Artificial Sequence: SFG-232R

SEQ ID No:17: Description of Artificial Sequence: SFG-239R

SEQ ID No:18: Description of Artificial Sequence: SFG-230R

SEQ ID No:23: Description of Artificial Sequence: sfgAL5

SEQ ID No:24: Description of Artificial Sequence: sfgAR4

SEQ ID No:25: Description of Artificial Sequence: sfgBL7

SEQ ID No:26: Description of Artificial Sequence: sfgBR3

What is claimed is:

1. An isolated polypeptide which is an enzyme having the activity of degrading β1-6 bonds and β1-4 bonds between D-sulfated galactose or galactose and D-sulfated galactose or galactose in a sulfated fucogalactan, which is selected from the group consisting of:
   (a) a polypeptide comprising the amino acid sequence of SEQ ID NO:28; and
   (b) a polypeptide encoded by a nucleic acid capable of hybridizing to the nucleotide sequence of SEQ ID NO:27 or a complete complementary strand thereof under the stringent conditions of 6×SSC (1×SSC: 0.1M NaCl, 0.015M sodium citrate, pH 7.0) containing 5× Denhardt's reagent, 0.5% SDS, 100 µg/ml denatured, fragmented salmon sperm DNA at 68° C. for 12-20 hours, and washing in 2×SSC containing 0.1% SDS at room temperature while changing the SSC concentration to 0.1×SSC and the temperature to 68° C.

* * * * *

SEQUENCE LISTING

```
<160> NUMBER OF SEQ ID NOS: 30

<210> SEQ ID NO 1
<211> LENGTH: 10
<212> TYPE: PRT
<213> ORGANISM: Flavobacterium
<220> FEATURE:
<221> NAME/KEY: PEPTIDE
<222> LOCATION: (1)..(10)

<400> SEQUENCE: 1

Lys Ile Ser Thr Gln Glu Gln Ala Asp Asn
1               5                   10
```

```
<210> SEQ ID NO 2
<211> LENGTH: 13
<212> TYPE: PRT
<213> ORGANISM: Flavobacterium
<220> FEATURE:
<221> NAME/KEY: PEPTIDE
<222> LOCATION: (1)..(13)

<400> SEQUENCE: 2

Lys Asn Leu Pro Val Trp Asp Ser Glu Val Asn His Asn
1               5                   10

<210> SEQ ID NO 3
<211> LENGTH: 21
<212> TYPE: PRT
<213> ORGANISM: Flavobacterium
<220> FEATURE:
<221> NAME/KEY: PEPTIDE
<222> LOCATION: (1)..(21)

<400> SEQUENCE: 3

Lys Thr Tyr Thr Thr Tyr Pro Asp Pro Thr Val Thr Ala Asp Ala Glu
1               5                   10                  15

Gly Ala Val Gly Gln
            20

<210> SEQ ID NO 4
<211> LENGTH: 21
<212> TYPE: PRT
<213> ORGANISM: Flavobacterium
<220> FEATURE:
<221> NAME/KEY: PEPTIDE
<222> LOCATION: (1)..(21)

<400> SEQUENCE: 4

Lys Trp Ile Asn Pro Phe Asn Glu Asp Gly Arg Ala Thr Asn Ser Thr
1               5                   10                  15

Trp Ser Val Asn Gln
            20

<210> SEQ ID NO 5
<211> LENGTH: 21
<212> TYPE: PRT
<213> ORGANISM: Flavobacterium
<220> FEATURE:
<221> NAME/KEY: PEPTIDE
<222> LOCATION: (1)..(21)

<400> SEQUENCE: 5

Lys Val Asp Gly Ile Val Leu Tyr Asp Ser Trp Arg Thr Ile Ser Leu
1               5                   10                  15

Thr Asp Gly Ser Ile
            20

<210> SEQ ID NO 6
<211> LENGTH: 21
<212> TYPE: PRT
<213> ORGANISM: Flavobacterium
<220> FEATURE:
<221> NAME/KEY: PEPTIDE
<222> LOCATION: (1)..(21)

<400> SEQUENCE: 6

Lys Asp Asn Val Asn Gly Ala Glu Leu Val Gly Pro Val Thr Ile Gly
1               5                   10                  15
```

Leu Pro Ala Ala Ile
        20

<210> SEQ ID NO 7
<211> LENGTH: 13
<212> TYPE: PRT
<213> ORGANISM: Flavobacterium
<220> FEATURE:
<221> NAME/KEY: PEPTIDE
<222> LOCATION: (1)..(13)

<400> SEQUENCE: 7

Lys Ser Ala Met Ser Asn Phe Thr Val Ser Val Ile Asn
1               5                   10

<210> SEQ ID NO 8
<211> LENGTH: 47
<212> TYPE: DNA
<213> ORGANISM: Artificial
<220> FEATURE:
<223> OTHER INFORMATION: NcoI cassete1

<400> SEQUENCE: 8
gtacatattg tcgttagaac gcgtaatacg actcactata gggagac           47

<210> SEQ ID NO 9
<211> LENGTH: 51
<212> TYPE: DNA
<213> ORGANISM: Artificial
<220> FEATURE:
<223> OTHER INFORMATION: NcoI cassete2

<400> SEQUENCE: 9
catggtctcc ctatagtgag tcgtattacg cgttctaacg acaatatgta c          51

<210> SEQ ID NO 10
<211> LENGTH: 20
<212> TYPE: DNA
<213> ORGANISM: Artificial
<220> FEATURE:
<223> OTHER INFORMATION: SFG-391F
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t

<400> SEQUENCE: 10
aagacntata cnacntaycc                                            20

<210> SEQ ID NO 11
<211> LENGTH: 23
<212> TYPE: DNA
<213> ORGANISM: Artificial
<220> FEATURE:
<223> OTHER INFORMATION: SFG-392F
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)

<223> OTHER INFORMATION: n is a, c, g, or t

<400> SEQUENCE: 11
gatcckackg tkacngcnga ygc                                              23

<210> SEQ ID NO 12
<211> LENGTH: 23
<212> TYPE: DNA
<213> ORGANISM: Artificial
<220> FEATURE:
<223> OTHER INFORMATION: SFG-421F
<220> FEATURE:
<221> NAME/KEY: misc_feature
<222> LOCATION: (15)..(15)
<223> OTHER INFORMATION: n is a, c, g, or t

<400> SEQUENCE: 12
aagtggatwa atccnttyaa yga                                              23

<210> SEQ ID NO 13
<211> LENGTH: 26
<212> TYPE: DNA
<213> ORGANISM: Artificial
<220> FEATURE:
<223> OTHER INFORMATION: SFG-422F
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 13
tttaatgagg atggdcgwgc nacnaa                                           26

<210> SEQ ID NO 14
<211> LENGTH: 26
<212> TYPE: DNA
<213> ORGANISM: Artificial
<220> FEATURE:
<223> OTHER INFORMATION: SFG-423F
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 14
tttaatgagg atggdagrgc nacnaa                                           26

<210> SEQ ID NO 15
<211> LENGTH: 24
<212> TYPE: DNA
<213> ORGANISM: Artificial
<220> FEATURE:
<223> OTHER INFORMATION: SFG-231R
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 15

```
gttgtggttn acttcngart ccca                                              24

<210> SEQ ID NO 16
<211> LENGTH: 24
<212> TYPE: DNA
<213> ORGANISM: Artificial
<220> FEATURE:
<223> OTHER INFORMATION: SFG-232R
<220> FEATURE:
<221> NAME/KEY: misc_feature
<222> LOCATION: (10)..(10)
<223> OTHER INFORMATION: n is a, c, g, or t

<400> SEQUENCE: 16
gttgtggttn acttcrctrt ccca                                              24

<210> SEQ ID NO 17
<211> LENGTH: 20
<212> TYPE: DNA
<213> ORGANISM: Artificial
<220> FEATURE:
<223> OTHER INFORMATION: SFG-239R
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 17
ttcngagtcc canacnggwa                                                   20

<210> SEQ ID NO 18
<211> LENGTH: 20
<212> TYPE: DNA
<213> ORGANISM: Artificial
<220> FEATURE:
<223> OTHER INFORMATION: SFG-230R
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 18
ttcrctgtcc canacnggha                                                   20

<210> SEQ ID NO 19
<211> LENGTH: 1602
<212> TYPE: DNA
<213> ORGANISM: Flavobacterium

<400> SEQUENCE: 19
atgaatttaa aaaattactc gataaaaaca ttatttctca ctttagttat ttattgcatc        60
aacacaacta tgtatggtca aaccactatc tataccaacg atatggatta tgtaattggt      120
gatgccaaac aagctttttat tcaaaataaa atatccactc aggaacaggc agacaattta     180
ttaaaagggt ttaaaaaaat gaaagtaaac gggatccgta tccctatttt ccctagagat      240
```

-continued

```
aaaaatactg gtgttgatat caatcctaac aaacctttga tggattattt ttatcaacaa      300
gcattggctc aagggttct tattttttgcc aacccagcac aaggtggtgg tggagcacgt      360
atcgccaaca attcattaga acatgaaggt ggtgttaata acgttcaggc agcaactgaa      420
gaattaattt atagagtttt agaattttct aatgaatatc cagattgtaa atggatcaac      480
cctttttaatg aagatggtag agctacaaat agtacttgga gtgtaaacca atatcatgct     540
atttattcaa cattaaaaga caacgtaaat ggagcagaat tagtaggacc ttgtacatgg      600
ggattacctg cagccattga tatgatgcaa aacacaaata tagctgacta catcactgta      660
gccacatcac ataatttagg ttttcatcat ggacaatggc caacatttat aaatctagcg      720
aaacaaaaaa acttacccgt ttgggattct gaagtaaacc ataatgacaa gtttggaaca      780
ggtactcgtt tagaaaaagc catagaaaac aaagtagacg gactagtgtt atacgactct      840
tggagaacta tcagtctaac ggatggttca ataagtaata gccaacaaga gaaatgtta      900
ctttacttaa aagactatac cattcctgtt agtattgcat aaacggaac tgctacacaa       960
tcttcaacaa accctaaatt taacaaggc ccagaacttg ccatagacgg aaacaccaat      1020
ggtaattacg gtggtggttc tgtaacagtt actaatggag aacaaaatgc atggtggcag     1080
gtagatttag gttctgaaca agaaatagga gaaattaagg tatttaacag aaccgatggt    1140
tgttgtaaga gtgcaatgtc taatttcaca gtatctgtta taaacagtaa aggcattaca    1200
acctatacta aaacatacac aacatatcca gatccaacgg taactgctga tgcagaaggt   1260
gcagtaggac aaattattaa agtacagtta aatgtagagg gtgccttaac cttagcagaa    1320
gttcaagtat ttgctccaga cacagattta tctacagaaa tttacaaact gattgatgtt    1380
aacatctttc ctaaccctac aactgataaa gtaacagtaa caactcctaa agaaaccttt    1440
aagaaattta ctttatacaa cactaacgga caaagtatat tgactaaaaa tgttaatact    1500
caagaattgg aaatcaacgt aagtaaactt acaaaaggga tatacatatt aaaacttgag   1560
ggtgatagat tttcaggaat tcataaaatt atcaaagaat aa                         1602
```

<210> SEQ ID NO 20
<211> LENGTH: 533
<212> TYPE: PRT
<213> ORGANISM: Flavobacterium

<400> SEQUENCE: 20

```
Met Asn Leu Lys Asn Tyr Ser Ile Lys Thr Leu Phe Leu Thr Leu Val
1               5                   10                  15

Ile Tyr Cys Ile Asn Thr Thr Met Tyr Gly Gln Thr Thr Ile Tyr Thr
            20                  25                  30

Asn Asp Met Asp Tyr Val Ile Gly Asp Ala Lys Gln Ala Phe Ile Gln
        35                  40                  45

Asn Lys Ile Ser Thr Gln Glu Gln Ala Asp Asn Leu Leu Lys Gly Phe
    50                  55                  60

Lys Lys Met Lys Val Asn Gly Ile Arg Ile Pro Ile Phe Pro Arg Asp
65                  70                  75                  80

Lys Asn Thr Gly Val Asp Ile Asn Pro Asn Lys Pro Leu Met Asp Tyr
                85                  90                  95

Phe Tyr Gln Gln Ala Leu Ala Gln Gly Phe Leu Ile Phe Ala Asn Pro
            100                 105                 110

Ala Gln Gly Gly Gly Gly Ala Arg Ile Ala Asn Asn Ser Leu Glu His
        115                 120                 125

Glu Gly Gly Val Asn Asn Val Gln Ala Ala Thr Glu Glu Leu Ile Tyr
```

```
            130                 135                 140
Arg Val Leu Glu Phe Ser Asn Glu Tyr Pro Asp Cys Lys Trp Ile Asn
145                 150                 155                 160

Pro Phe Asn Glu Asp Gly Arg Ala Thr Asn Ser Thr Trp Ser Val Asn
            165                 170                 175

Gln Tyr His Ala Ile Tyr Ser Thr Leu Lys Asp Asn Val Asn Gly Ala
                180                 185                 190

Glu Leu Val Gly Pro Cys Thr Trp Gly Leu Pro Ala Ala Ile Asp Met
            195                 200                 205

Met Gln Asn Thr Asn Ile Ala Asp Tyr Ile Thr Val Ala Thr Ser His
210                 215                 220

Asn Leu Gly Phe His His Gly Gln Trp Pro Thr Phe Ile Asn Leu Ala
225                 230                 235                 240

Lys Gln Lys Asn Leu Pro Val Trp Asp Ser Glu Val Asn His Asn Asp
                245                 250                 255

Lys Phe Gly Thr Gly Thr Arg Leu Glu Lys Ala Ile Glu Asn Lys Val
            260                 265                 270

Asp Gly Leu Val Leu Tyr Asp Ser Trp Arg Thr Ile Ser Leu Thr Asp
            275                 280                 285

Gly Ser Ile Ser Asn Ser Gln Gln Glu Glu Met Leu Leu Tyr Leu Lys
            290                 295                 300

Asp Tyr Thr Ile Pro Val Ser Ile Ala Leu Asn Gly Thr Ala Thr Gln
305                 310                 315                 320

Ser Ser Thr Asn Pro Lys Phe Asn Lys Gly Pro Glu Leu Ala Ile Asp
                325                 330                 335

Gly Asn Thr Asn Gly Asn Tyr Gly Gly Ser Val Thr Val Thr Asn
            340                 345                 350

Gly Glu Gln Asn Ala Trp Trp Gln Val Asp Leu Gly Ser Glu Gln Glu
                355                 360                 365

Ile Gly Glu Ile Lys Val Phe Asn Arg Thr Asp Gly Cys Cys Lys Ser
            370                 375                 380

Ala Met Ser Asn Phe Thr Val Ser Val Ile Asn Ser Lys Gly Ile Thr
385                 390                 395                 400

Thr Tyr Thr Lys Thr Tyr Thr Thr Tyr Pro Asp Pro Thr Val Thr Ala
                405                 410                 415

Asp Ala Glu Gly Ala Val Gly Gln Ile Ile Lys Val Gln Leu Asn Val
            420                 425                 430

Glu Gly Ala Leu Thr Leu Ala Glu Val Gln Val Phe Ala Pro Asp Thr
            435                 440                 445

Asp Leu Ser Thr Glu Ile Tyr Lys Leu Ile Asp Val Asn Ile Phe Pro
450                 455                 460

Asn Pro Thr Thr Asp Lys Val Thr Val Thr Thr Pro Lys Glu Thr Phe
465                 470                 475                 480

Lys Lys Phe Thr Leu Tyr Asn Thr Asn Gly Gln Ser Ile Leu Thr Lys
                485                 490                 495

Asn Val Asn Thr Gln Glu Leu Glu Ile Asn Val Ser Lys Leu Thr Lys
            500                 505                 510

Gly Ile Tyr Ile Leu Lys Leu Glu Gly Asp Arg Phe Ser Gly Ile His
            515                 520                 525

Lys Ile Ile Lys Glu
    530

<210> SEQ ID NO 21
```

<211> LENGTH: 1626
<212> TYPE: DNA
<213> ORGANISM: Flavobacterium

<400> SEQUENCE: 21

```
atgaaccccc attcaatgaa ttcgaaaaaa tattacgtat caaaaataaa attattaaac      60
tacatcttta tctgctgttc atgcattact atgtttggtc aaaacatata cactaatgat     120
atggattatg tattaggaga tactaaacaa cgttttatta ctggagccgt aaaaatata      180
gaacaagcag acaacctttt aaagggtttt aaagcaatga agtaaatgg aatccgtatc      240
ccaattttcc ctagagataa aaatactggt gctgatatca atcctaacaa accagtgatg     300
gattattttt atgaacaagc tctagcacaa gggtttctta tttttgcaaa tccagcgcaa     360
ggaggtggtg gtattagaat agcaaatcac tcactaacca cactaactc tgtaaacggt      420
aaacaagaag ctactgatga gctagttaat agaattattg aattttctaa cgaatatcca     480
gactgtaaat ggatcaaccc ttttaacgaa acggtagag ctacaaacag tacatggagc      540
atcagtcaaa taatgaaat ttaccaaaga ttacacacac acggattaaa tggtgcagaa      600
ttaatagggc cttgcacatg gggattacca gcaggtatag atatgttaca aaacacaaaa     660
atagccgact atattactgt ggcatcttct cacaatcttg gtcatcatga ccatttatgg     720
gatgatttta gagcattggc agatcaagaa aatttacctg tttgggactc tgaagcaaat     780
aacgatccag gaatacaga tacgaataaa gtagaagcgg ctatagcaaa taaagtagat      840
ggtttggtag tttacaactc aggaaataat ataaatttaa attcaggatc tcttacgact     900
accaactatt attatatgtc taagtattta aaacctagaa ctaatcttgc gttaaatggt     960
attgctacac aatcagaaac tacatctcca caatttaact tagaggcttc tcgtgctatt    1020
gatgataata tagccggtag ttatgctggt ggtaatggat ctatttctca tacttctggt    1080
acaaatccat ggtggcaagt agatcttggt gctgaaaaaa aaattgaaga gatctatatc    1140
tttaacagaa cagataacgg tactaaagaa aacctttcca atttttacaat aacggttaca    1200
aatactaatg tgttacagtt tttaatgaa acgtatgctg aatatccaga tccagcccttt    1260
atcattgaaa caggacttat aacaggtcgt attgttaaaa ttcaaatcaa tgcaactaga    1320
gcattaacat tagcagaagt acaagttttt gctccaaaag aaagtttatc tacaaaaatc    1380
taccataaaa ttaatacccca cttacataac aatcctgtaa cagatatatt aaaagtaagt    1440
gctattaatg agaatgatgt atttaaaaaa tatactttat attacaccaa tggacaagta    1500
attacaacca aaaatactaa tacaaaagaa ctagaaataa atgtaagtca tcttccaaca    1560
gatatctatt tccttaaagt agaaggtgat caattttctg aacccataa aatcatcaaa    1620
aaataa                                                                1626
```

<210> SEQ ID NO 22
<211> LENGTH: 541
<212> TYPE: PRT
<213> ORGANISM: Flavobacterium

<400> SEQUENCE: 22

```
Met Asn Pro His Ser Met Asn Ser Lys Lys Tyr Tyr Val Ser Lys Ile
1               5                   10                  15

Lys Leu Leu Asn Tyr Ile Phe Ile Cys Cys Ser Cys Ile Thr Met Phe
            20                  25                  30

Gly Gln Asn Ile Tyr Thr Asn Asp Met Asp Tyr Val Leu Gly Asp Thr
        35                  40                  45
```

-continued

```
Lys Gln Arg Phe Ile Thr Gly Ala Val Lys Asn Ile Glu Gln Ala Asp
     50                  55                  60

Asn Leu Leu Lys Gly Phe Lys Ala Met Lys Val Asn Gly Ile Arg Ile
 65                  70                  75                  80

Pro Ile Phe Pro Arg Asp Lys Asn Thr Gly Ala Asp Ile Asn Pro Asn
                 85                  90                  95

Lys Pro Val Met Asp Tyr Phe Tyr Glu Gln Ala Leu Ala Gln Gly Phe
                100                 105                 110

Leu Ile Phe Ala Asn Pro Ala Gln Gly Gly Gly Ile Arg Ile Ala
            115                 120                 125

Asn His Ser Leu Thr Asn Thr Asn Ser Val Asn Gly Lys Gln Glu Ala
            130                 135                 140

Thr Asp Glu Leu Val Asn Arg Ile Ile Glu Phe Ser Asn Glu Tyr Pro
145                 150                 155                 160

Asp Cys Lys Trp Ile Asn Pro Phe Asn Glu Asp Gly Arg Ala Thr Asn
                165                 170                 175

Ser Thr Trp Ser Ile Ser Gln Ile Asn Glu Ile Tyr Gln Arg Leu His
            180                 185                 190

Thr His Gly Leu Asn Gly Ala Glu Leu Ile Gly Pro Cys Thr Trp Gly
            195                 200                 205

Leu Pro Ala Gly Ile Asp Met Leu Gln Asn Thr Lys Ile Ala Asp Tyr
210                 215                 220

Ile Thr Val Ala Ser His Asn Leu Gly His His Asp His Leu Trp
225                 230                 235                 240

Asp Asp Phe Arg Ala Leu Ala Asp Gln Glu Asn Leu Pro Val Trp Asp
                245                 250                 255

Ser Glu Ala Asn Asn Asp Pro Gly Asn Thr Asp Thr Asn Lys Val Glu
            260                 265                 270

Ala Ala Ile Ala Asn Lys Val Asp Gly Leu Val Val Tyr Asn Ser Gly
            275                 280                 285

Asn Asn Ile Asn Leu Asn Ser Gly Ser Leu Thr Thr Thr Asn Tyr Tyr
290                 295                 300

Tyr Met Ser Lys Tyr Leu Lys Pro Arg Thr Asn Leu Ala Leu Asn Gly
305                 310                 315                 320

Ile Ala Thr Gln Ser Glu Thr Thr Ser Pro Gln Phe Asn Leu Glu Ala
                325                 330                 335

Ser Arg Ala Ile Asp Asp Asn Ile Ala Gly Ser Tyr Ala Gly Gly Asn
            340                 345                 350

Gly Ser Ile Ser His Thr Ser Gly Thr Asn Pro Trp Trp Gln Val Asp
            355                 360                 365

Leu Gly Ala Glu Lys Lys Ile Glu Glu Ile Tyr Ile Phe Asn Arg Thr
370                 375                 380

Asp Asn Gly Thr Lys Glu Asn Leu Ser Asn Phe Thr Ile Thr Val Thr
385                 390                 395                 400

Asn Thr Asn Gly Val Thr Val Phe Asn Glu Thr Tyr Ala Glu Tyr Pro
                405                 410                 415

Asp Pro Ala Leu Ile Ile Glu Thr Gly Leu Ile Thr Gly Arg Ile Val
            420                 425                 430

Lys Ile Gln Ile Asn Ala Thr Arg Ala Leu Thr Leu Ala Glu Val Gln
            435                 440                 445

Val Phe Ala Pro Lys Glu Ser Leu Ser Thr Lys Ile Tyr His Lys Ile
450                 455                 460

Asn Thr His Leu His Asn Asn Pro Val Thr Asp Ile Leu Lys Val Ser
```

```
                465                 470                 475                 480
Ala Ile Asn Glu Asn Asp Val Phe Lys Lys Tyr Thr Leu Tyr Tyr Thr
                    485                 490                 495

Asn Gly Gln Val Ile Thr Thr Lys Asn Thr Asn Thr Lys Glu Leu Glu
            500                 505                 510

Ile Asn Val Ser His Leu Pro Thr Asp Ile Tyr Phe Leu Lys Val Glu
        515                 520                 525

Gly Asp Gln Phe Ser Gly Thr His Lys Ile Ile Lys Lys
    530                 535                 540

<210> SEQ ID NO 23
<211> LENGTH: 31
<212> TYPE: DNA
<213> ORGANISM: Artificial
<220> FEATURE:
<223> OTHER INFORMATION: sfgAL5

<400> SEQUENCE: 23
gcatcaacac acatatgtat ggtcaaacca c                                 31

<210> SEQ ID NO 24
<211> LENGTH: 38
<212> TYPE: DNA
<213> ORGANISM: Artificial
<220> FEATURE:
<223> OTHER INFORMATION: sfgAR4

<400> SEQUENCE: 24
ccttttttta attactcgag ttctttgata attttatg                          38

<210> SEQ ID NO 25
<211> LENGTH: 32
<212> TYPE: DNA
<213> ORGANISM: Artificial
<220> FEATURE:
<223> OTHER INFORMATION: sfgBL7

<400> SEQUENCE: 25
gctgttcatg cattcatatg tttggtcaaa ac                                32

<210> SEQ ID NO 26
<211> LENGTH: 36
<212> TYPE: DNA
<213> ORGANISM: Artificial
<220> FEATURE:
<223> OTHER INFORMATION: sfgBR3

<400> SEQUENCE: 26
ttagtagtta ctcgagtttt ttgatgattt tatggg                            36

<210> SEQ ID NO 27
<211> LENGTH: 1533
<212> TYPE: DNA
<213> ORGANISM: Flavobacterium sp.

<400> SEQUENCE: 27
atgtatggtc aaaccactat ctataccaac gatatggatt atgtaattgg tgatgccaaa      60
caagctttta ttcaaaataa aatatccact caggaacagg cagacaattt attaaaaggg     120
tttaaaaaaa tgaaagtaaa cgggatccgt atccctattt tccctagaga taaaaatact     180
ggtgttgata tcaatcctaa caaacctttg atggattatt ttatcaaca agcattggct     240 caagggtttc ttattttttgc caacccagca caaggtggtg gtggagcacg tatcgccaac     300
```

-continued

```
aattcattag aacatgaagg tggtgttaat aacgttcagg cagcaactga agaattaatt    360
tatagagttt tagaattttc taatgaatat ccagattgta aatggatcaa ccctttaat     420 gaagatggta gagctacaaa tagtacttgg agtgtaaacc aatatcatgc tatttattca    480
acattaaaag acaacgtaaa tggagcagaa ttagtaggac cttgtacatg gggattacct    540
gcagccattg atatgatgca aaacacaaat atagctgact acatcactgt agccacatca    600
cataatttag gttttcatca tggacaatgg ccaacattta taaatctagc gaaacaaaaa    660
aacttacccg tttgggattc tgaagtaaac cataatgaca agtttggaac aggtactcgt    720
ttagaaaaag ccatagaaaa caaagtagac ggactagtgt tatacgactc ttggagaact    780
atcagtctaa cggatggttc aataagtaat agccaacaag aagaaatgtt actttactta    840
aaagactata ccattcctgt tagtattgca ttaaacggaa ctgctacaca atcttcaaca    900
aaccctaaat ttaacaaagg cccagaactt gccatagacg aaacaccaa tggtaattac     960 ggtggtggtt ctgtaacagt tactaatgga gaacaaaatg catggtggca ggtagattta   1020
ggttctgaac aagaaatagg agaaattaag gtatttaaca gaaccgatgg ttgttgtaag   1080
agtgcaatgt ctaatttcac agtatctgtt ataaacagta aaggcattac aacctatact   1140
aaaacataca caacatatcc agatccaacg gtaactgctg atgcagaagg tgcagtagga   1200
caaattatta agtacagtt aaatgtagag ggtgccttaa ccttagcaga agttcaagta    1260
tttgctccag acacagattt atctacagaa atttacaaac tgattgatgt taacatcttt   1320
cctaacccta caactgataa agtaacagta acaactccta agaaaccctt taagaaattt   1380
actttataca acactaacgg acaaagtata ttgactaaaa atgttaatac tcaagaattg   1440
gaaatcaacg taagtaaact tacaaaaggg atatacatat taaaacttga gggtgataga   1500
ttttcaggaa ttcataaaat tatcaaagaa taa                                1533
```

<210> SEQ ID NO 28
<211> LENGTH: 510
<212> TYPE: PRT
<213> ORGANISM: Flavobacterium sp.

<400> SEQUENCE: 28

```
Met Tyr Gly Gln Thr Thr Ile Tyr Thr Asn Asp Met Asp Tyr Val Ile
1               5                   10                  15

Gly Asp Ala Lys Gln Ala Phe Ile Gln Asn Lys Ile Ser Thr Gln Glu
            20                  25                  30

Gln Ala Asp Asn Leu Leu Lys Gly Phe Lys Lys Met Lys Val Asn Gly
        35                  40                  45

Ile Arg Ile Pro Ile Phe Pro Arg Asp Lys Asn Thr Gly Val Asp Ile
    50                  55                  60

Asn Pro Asn Lys Pro Leu Met Asp Tyr Phe Gln Gln Ala Leu Ala
65                  70                  75                  80

Gln Gly Phe Leu Ile Phe Ala Asn Pro Ala Gln Gly Gly Gly Ala
                85                  90                  95

Arg Ile Ala Asn Asn Ser Leu Glu His Glu Gly Val Asn Asn Val
            100                 105                 110

Gln Ala Ala Thr Glu Glu Leu Ile Tyr Arg Val Leu Glu Phe Ser Asn
        115                 120                 125

Glu Tyr Pro Asp Cys Lys Trp Ile Asn Pro Phe Asn Glu Asp Gly Arg
    130                 135                 140

Ala Thr Asn Ser Thr Trp Ser Val Asn Gln Tyr His Ala Ile Tyr Ser
```

```
                    145                 150                 155                 160
Thr Leu Lys Asp Asn Val Asn Gly Ala Glu Leu Val Gly Pro Cys Thr
                165                 170                 175

Trp Gly Leu Pro Ala Ala Ile Asp Met Met Gln Asn Thr Asn Ile Ala
            180                 185                 190

Asp Tyr Ile Thr Val Ala Thr Ser His Asn Leu Gly Phe His His Gly
        195                 200                 205

Gln Trp Pro Thr Phe Ile Asn Leu Ala Lys Gln Lys Asn Leu Pro Val
    210                 215                 220

Trp Asp Ser Glu Val Asn His Asn Asp Lys Phe Gly Thr Gly Thr Arg
225                 230                 235                 240

Leu Glu Lys Ala Ile Glu Asn Lys Val Asp Gly Leu Val Leu Tyr Asp
                245                 250                 255

Ser Trp Arg Thr Ile Ser Leu Thr Asp Gly Ser Ile Ser Asn Ser Gln
            260                 265                 270

Gln Glu Glu Met Leu Leu Tyr Leu Lys Asp Tyr Thr Ile Pro Val Ser
        275                 280                 285

Ile Ala Leu Asn Gly Thr Ala Thr Gln Ser Ser Thr Asn Pro Lys Phe
    290                 295                 300

Asn Lys Gly Pro Glu Leu Ala Ile Asp Gly Asn Thr Asn Gly Asn Tyr
305                 310                 315                 320

Gly Gly Gly Ser Val Thr Val Thr Asn Gly Glu Gln Asn Ala Trp Trp
                325                 330                 335

Gln Val Asp Leu Gly Ser Glu Gln Glu Ile Gly Glu Ile Lys Val Phe
            340                 345                 350

Asn Arg Thr Asp Gly Cys Cys Lys Ser Ala Met Ser Asn Phe Thr Val
        355                 360                 365

Ser Val Ile Asn Ser Lys Gly Ile Thr Thr Tyr Thr Lys Thr Tyr Thr
    370                 375                 380

Thr Tyr Pro Asp Pro Thr Val Thr Ala Asp Ala Glu Gly Ala Val Gly
385                 390                 395                 400

Gln Ile Ile Lys Val Gln Leu Asn Val Glu Gly Ala Leu Thr Leu Ala
                405                 410                 415

Glu Val Gln Val Phe Ala Pro Asp Thr Asp Leu Ser Thr Glu Ile Tyr
            420                 425                 430

Lys Leu Ile Asp Val Asn Ile Phe Pro Asn Pro Thr Thr Asp Lys Val
        435                 440                 445

Thr Val Thr Thr Pro Lys Glu Thr Phe Lys Lys Phe Thr Leu Tyr Asn
    450                 455                 460

Thr Asn Gly Gln Ser Ile Leu Thr Lys Asn Val Asn Thr Gln Glu Leu
465                 470                 475                 480

Glu Ile Asn Val Ser Lys Leu Thr Lys Gly Ile Tyr Ile Leu Lys Leu
                485                 490                 495

Glu Gly Asp Arg Phe Ser Gly Ile His Lys Ile Ile Lys Glu
            500                 505                 510

<210> SEQ ID NO 29
<211> LENGTH: 1536
<212> TYPE: DNA
<213> ORGANISM: Flavobacterium sp.

<400> SEQUENCE: 29
atgtttggtc aaaacatata cactaatgat atggattatg tattaggaga tactaaacaa      60
cgttttatta ctggagccgt taaaaatata gaacaagcag acaacctttt aaaagggttt     120
```

-continued

```
aaagcaatga aagtaaatgg aatccgtatc ccaattttcc ctagagataa aaatactggt    180
gctgatatca atcctaacaa accagtgatg gattatttt atgaacaagc tctagcacaa    240
gggtttctta tttttgcaaa tccagcgcaa ggaggtggtg gtattagaat agcaaatcac    300
tcactaacca acactaactc tgtaaacggt aaacaagaag ctactgatga gctagttaat    360
agaattattg aattttctaa cgaatatcca gactgtaaat ggatcaaccc ttttaacgaa    420
gacggtagag ctacaaacag tacatggagc atcagtcaaa taatgaaat ttaccaaaga    480
ttacacacac acggattaaa tggtgcagaa ttaatagggc cttgcacatg gggattacca    540
gcaggtatag atatgttaca aaacacaaaa atagccgact atattactgt ggcatcttct    600
cacaatcttg gtcatcatga ccatttatgg gatgatttta gagcattggc agatcaagaa    660
aatttacctg tttgggactc tgaagcaaat aacgatccag ggaatacaga tacgaataaa    720
gtagaagcgg ctatagcaaa taagtagat ggtttggtag tttacaactc aggaaataat    780
ataaatttaa attcaggatc tcttacgact accaactatt attatatgtc taagtattta    840
aaacctagaa ctaatcttgc gttaaatggt attgctacac aatcagaaac tacatctcca    900
caatttaact tagaggcttc tcgtgctatt gatgataata tagccggtag ttatgctggt    960
ggtaatggat ctatttctca tacttctggt acaaatccat ggtggcaagt agatcttggt   1020
gctgaaaaaa aaattgaaga gatctatatc tttaacagaa cagataacgg tactaaagaa   1080
aacctttcca attttacaat aacggttaca aatactaatg gtgttacagt ttttaatgaa   1140
acgtatgctg aatatccaga tccagcccct atcattgaaa caggacttat aacaggtcgt   1200
attgttaaaa ttcaaatcaa tgcaactaga gcattaacat tagcagaagt acaagttttt   1260
gctccaaaag aaagtttatc tacaaaaatc taccataaaa ttaataccca cttacataac   1320
aatcctgtaa cagatatatt aaaagtaagt gctattaatg agaatgatgt atttaaaaaa   1380
tatactttat attaccaccaa tggacaagta attacaacca aaaatactaa tacaaaagaa   1440
ctagaaataa atgtaagtca tcttccaaca gatatctatt tccttaaagt agaaggtgat   1500
caattttctg gaacccataa aatcatcaaa aaataa                             1536
```

<210> SEQ ID NO 30
<211> LENGTH: 511
<212> TYPE: PRT
<213> ORGANISM: Flavobacterium sp.

<400> SEQUENCE: 30

```
Met Phe Gly Gln Asn Ile Tyr Thr Asn Asp Met Asp Tyr Val Leu Gly
1               5                   10                  15

Asp Thr Lys Gln Arg Phe Ile Thr Gly Ala Val Lys Asn Ile Glu Gln
            20                  25                  30

Ala Asp Asn Leu Leu Lys Gly Phe Lys Ala Met Lys Val Asn Gly Ile
        35                  40                  45

Arg Ile Pro Ile Phe Pro Arg Asp Lys Asn Thr Gly Ala Asp Ile Asn
    50                  55                  60

Pro Asn Lys Pro Val Met Asp Tyr Phe Tyr Glu Gln Ala Leu Ala Gln
65                  70                  75                  80

Gly Phe Leu Ile Phe Ala Asn Pro Ala Gln Gly Gly Gly Ile Arg
                85                  90                  95

Ile Ala Asn His Ser Leu Thr Asn Thr Asn Ser Val Asn Gly Lys Gln
            100                 105                 110

Glu Ala Thr Asp Glu Leu Val Asn Arg Ile Ile Glu Phe Ser Asn Glu
```

```
            115                 120                 125
Tyr Pro Asp Cys Lys Trp Ile Asn Pro Phe Asn Glu Asp Gly Arg Ala
    130                 135                 140

Thr Asn Ser Thr Trp Ser Ile Ser Gln Ile Asn Glu Ile Tyr Gln Arg
145                 150                 155                 160

Leu His Thr His Gly Leu Asn Gly Ala Glu Leu Ile Gly Pro Cys Thr
                165                 170                 175

Trp Gly Leu Pro Ala Gly Ile Asp Met Leu Gln Asn Thr Lys Ile Ala
            180                 185                 190

Asp Tyr Ile Thr Val Ala Ser Ser His Asn Leu Gly His His Asp His
                195                 200                 205

Leu Trp Asp Asp Phe Arg Ala Leu Ala Asp Gln Glu Asn Leu Pro Val
    210                 215                 220

Trp Asp Ser Glu Ala Asn Asn Asp Pro Gly Asn Thr Asp Thr Asn Lys
225                 230                 235                 240

Val Glu Ala Ala Ile Ala Asn Lys Val Asp Gly Leu Val Val Tyr Asn
                245                 250                 255

Ser Gly Asn Asn Ile Asn Leu Asn Ser Gly Ser Leu Thr Thr Thr Asn
            260                 265                 270

Tyr Tyr Tyr Met Ser Lys Tyr Leu Lys Pro Arg Thr Asn Leu Ala Leu
                275                 280                 285

Asn Gly Ile Ala Thr Gln Ser Glu Thr Thr Ser Pro Gln Phe Asn Leu
    290                 295                 300

Glu Ala Ser Arg Ala Ile Asp Asp Asn Ile Ala Gly Ser Tyr Ala Gly
305                 310                 315                 320

Gly Asn Gly Ser Ile Ser His Thr Ser Gly Thr Asn Pro Trp Trp Gln
                325                 330                 335

Val Asp Leu Gly Ala Glu Lys Lys Ile Glu Glu Ile Tyr Ile Phe Asn
            340                 345                 350

Arg Thr Asp Asn Gly Thr Lys Glu Asn Leu Ser Asn Phe Thr Ile Thr
    355                 360                 365

Val Thr Asn Thr Asn Gly Val Thr Val Phe Asn Glu Thr Tyr Ala Glu
370                 375                 380

Tyr Pro Asp Pro Ala Leu Ile Ile Glu Thr Gly Leu Ile Thr Gly Arg
385                 390                 395                 400

Ile Val Lys Ile Gln Ile Asn Ala Thr Arg Ala Leu Thr Leu Ala Glu
                405                 410                 415

Val Gln Val Phe Ala Pro Lys Glu Ser Leu Ser Thr Lys Ile Tyr His
            420                 425                 430

Lys Ile Asn Thr His Leu His Asn Asn Pro Val Thr Asp Ile Leu Lys
    435                 440                 445

Val Ser Ala Ile Asn Glu Asn Asp Val Phe Lys Lys Tyr Thr Leu Tyr
450                 455                 460

Tyr Thr Asn Gly Gln Val Ile Thr Thr Lys Asn Thr Asn Thr Lys Glu
465                 470                 475                 480

Leu Glu Ile Asn Val Ser His Leu Pro Thr Asp Ile Tyr Phe Leu Lys
                485                 490                 495

Val Glu Gly Asp Gln Phe Ser Gly Thr His Lys Ile Ile Lys Lys
            500                 505                 510
```